United States Patent
Voss et al.

(10) Patent No.: US 9,138,214 B2
(45) Date of Patent: Sep. 22, 2015

(54) SUTURE SECURING SYSTEMS, DEVICES AND METHODS

(75) Inventors: Laveille Kao Voss, Belmont, CA (US); Aaron M. Fortson, Fremont, CA (US); Douglas H. Mehl, Redwood City, CA (US); Rizza Garcia, Newark, CA (US); Wouter E. Roorda, Palo Alto, CA (US)

(73) Assignee: ABBOTT CARDIOVASCULAR SYSTEMS, INC., Santa Clara, CA (US)

( * ) Notice: Subject to any disclaimer, the term of this patent is extended or adjusted under 35 U.S.C. 154(b) by 761 days.

(21) Appl. No.: 13/411,320

(22) Filed: Mar. 2, 2012

(65) Prior Publication Data

US 2013/0231701 A1 Sep. 5, 2013

(51) Int. Cl.
*A61B 17/04* (2006.01)
*A61B 17/00* (2006.01)
*A61B 17/12* (2006.01)
*A61B 17/06* (2006.01)

(52) U.S. Cl.
CPC ......... *A61B 17/0057* (2013.01); *A61B 17/0467* (2013.01); *A61B 17/0485* (2013.01); *A61B 17/0487* (2013.01); *A61B 17/12136* (2013.01); *A61B 2017/00654* (2013.01); *A61B 2017/00663* (2013.01); *A61B 2017/0417* (2013.01); *A61B 2017/0454* (2013.01); *A61B 2017/0461* (2013.01); *A61B 2017/0464* (2013.01); *A61B 2017/06176* (2013.01)

(58) Field of Classification Search
CPC ........... A61B 17/0401; A61B 17/0467; A61B 17/0485; A61B 17/0057; A61B 2017/0404; A61B 2017/0409; A61B 2017/0414; A61B 2017/0446; A61B 2017/0448; A61B 2017/0451; A61B 2017/045; A61B 2017/0454; A61B 2017/0456; A61B 2017/0458; A61B 2017/0459; A61B 2017/0461; A61B 2017/00654; A61B 2017/0467; A61B 2017/0462

See application file for complete search history.

(56) References Cited

U.S. PATENT DOCUMENTS

| 2,238,563 A | 4/1941 | Jacques |
| 2,416,260 A * | 2/1947 | Karle ............................. 606/148 |

(Continued)

FOREIGN PATENT DOCUMENTS

| WO | WO 02/15795 | 2/2002 |
| WO | WO 2005/027754 | 3/2005 |

OTHER PUBLICATIONS

U.S. Appl. No. 12/917,195, May 6, 2013, Office Action.

(Continued)

*Primary Examiner* — Ryan Severson
(74) *Attorney, Agent, or Firm* — Workman Nydegger; Randy Shen

(57) ABSTRACT

A suture securing system is provided for use in closing a vessel puncture site while eliminating the need for sutures to be manually tied in knots. The system may include an elongate body comprising a shaft and a barrel slidably mounted on the shaft. A knot replacement element may include an outer surface and an inner lumen configured to receive suture lengths. The knot replacement element may be at least partially positioned within the distal end of the barrel adjacent to the distal portion of the shaft and may be configured to selectively fasten the suture lengths together over the vessel repair site. The system may also include a snare configured to draw the suture lengths through the knot replacement element and at least a portion of the elongate body. A trimmer member may be configured to selectively trim the suture lengths extending from the knot replacement element.

37 Claims, 24 Drawing Sheets

(56) References Cited

U.S. PATENT DOCUMENTS

| | | | |
|---|---|---|---|
| 2,449,235 A | 9/1948 | Krupp | |
| 3,766,610 A | 10/1973 | Thorsbakken | |
| 3,877,434 A * | 4/1975 | Ferguson et al. | 606/158 |
| 4,156,574 A | 5/1979 | Boden | |
| 4,705,040 A * | 11/1987 | Mueller et al. | 606/108 |
| 4,750,492 A * | 6/1988 | Jacobs | 606/230 |
| 4,807,333 A | 2/1989 | Boden | |
| 5,292,332 A | 3/1994 | Lee | |
| 5,342,393 A | 8/1994 | Stack | |
| 5,364,408 A * | 11/1994 | Gordon | 606/144 |
| 5,383,905 A * | 1/1995 | Golds et al. | 606/232 |
| 5,391,200 A | 2/1995 | KenKnight et al. | |
| 5,435,044 A | 7/1995 | Ida | |
| 5,454,140 A | 10/1995 | Murai | |
| 5,462,558 A * | 10/1995 | Kolesa et al. | 606/139 |
| 5,478,353 A | 12/1995 | Yoon | |
| 5,501,692 A * | 3/1996 | Riza | 606/148 |
| 5,507,754 A * | 4/1996 | Green et al. | 606/139 |
| 5,520,070 A | 5/1996 | Beugelsdyk et al. | |
| 5,520,702 A | 5/1996 | Sauer et al. | |
| 5,562,688 A * | 10/1996 | Riza | 606/148 |
| 5,562,689 A | 10/1996 | Green et al. | |
| 5,569,306 A | 10/1996 | Thai | |
| 5,572,770 A | 11/1996 | Boden | |
| 5,575,800 A * | 11/1996 | Gordon | 606/144 |
| 5,584,861 A | 12/1996 | Swain et al. | |
| 5,613,974 A | 3/1997 | Andreas et al. | |
| 5,630,824 A | 5/1997 | Hart | |
| 5,645,553 A * | 7/1997 | Kolesa et al. | 606/157 |
| 5,658,313 A | 8/1997 | Thal | |
| 5,662,664 A * | 9/1997 | Gordon et al. | 606/144 |
| 5,700,272 A * | 12/1997 | Gordon et al. | 606/144 |
| 5,702,397 A | 12/1997 | Goble et al. | |
| 5,725,529 A | 3/1998 | Nicholson et al. | |
| 5,779,707 A | 7/1998 | Bertholet et al. | |
| 5,868,762 A * | 2/1999 | Cragg et al. | 606/144 |
| 5,893,856 A | 4/1999 | Jacob et al. | |
| 5,899,921 A | 5/1999 | Caspari et al. | |
| 5,941,901 A | 8/1999 | Egan | |
| 6,066,160 A | 5/2000 | Colvin et al. | |
| 6,086,608 A | 7/2000 | Ek et al. | |
| 6,099,547 A | 8/2000 | Gellman et al. | |
| 6,190,414 B1 | 2/2001 | Young et al. | |
| 6,200,329 B1 | 3/2001 | Fung et al. | |
| 6,203,554 B1 * | 3/2001 | Roberts | 606/144 |
| 6,206,895 B1 | 3/2001 | Levinson | |
| 6,228,096 B1 * | 5/2001 | Marchand | 606/139 |
| 6,231,592 B1 | 5/2001 | Bonutti et al. | |
| 6,245,080 B1 | 6/2001 | Levinson | |
| 6,277,140 B2 | 8/2001 | Ginn et al. | |
| 6,398,796 B2 | 6/2002 | Levinson | |
| 6,475,230 B1 | 11/2002 | Bonutti et al. | |
| 6,712,837 B2 * | 3/2004 | Åkerfeldt et al. | 606/213 |
| 6,746,457 B2 * | 6/2004 | Dana et al. | 606/148 |
| 6,786,915 B2 * | 9/2004 | Akerfeldt et al. | 606/232 |
| 7,033,370 B2 * | 4/2006 | Gordon et al. | 606/144 |
| 7,060,077 B2 * | 6/2006 | Gordon et al. | 606/144 |
| 7,147,646 B2 * | 12/2006 | Dana et al. | 606/148 |
| 7,320,693 B2 * | 1/2008 | Pollack et al. | 606/144 |
| 7,361,183 B2 * | 4/2008 | Ginn | 606/194 |
| 7,390,328 B2 * | 6/2008 | Modesitt | 606/144 |
| 7,435,251 B2 * | 10/2008 | Green | 606/232 |
| 7,662,161 B2 | 2/2010 | Briganti et al. | |
| 7,713,284 B2 | 5/2010 | Crofford | |
| 7,842,051 B2 * | 11/2010 | Dana et al. | 606/148 |
| 7,875,043 B1 * | 1/2011 | Ashby et al. | 606/148 |
| 7,931,670 B2 * | 4/2011 | Fiehler et al. | 606/213 |
| 7,947,062 B2 | 5/2011 | Chin et al. | |
| 8,048,108 B2 * | 11/2011 | Sibbitt et al. | 606/213 |
| 8,100,923 B2 | 1/2012 | Paraschac et al. | |
| 8,128,652 B2 * | 3/2012 | Paprocki | 606/213 |
| 8,128,653 B2 | 3/2012 | McGuckin, Jr. et al. | |
| 8,262,736 B2 | 9/2012 | Michelson | |
| 8,337,522 B2 * | 12/2012 | Ditter | 606/213 |
| 8,480,691 B2 * | 7/2013 | Dana et al. | 606/148 |
| 8,579,934 B2 * | 11/2013 | Ginn | 606/213 |
| 8,647,364 B2 * | 2/2014 | Fiehler et al. | 606/213 |
| 8,932,324 B2 * | 1/2015 | Sibbitt et al. | 606/213 |
| 8,932,327 B2 * | 1/2015 | Kosa et al. | 606/228 |
| 2001/0023352 A1 * | 9/2001 | Gordon et al. | 606/144 |
| 2001/0044638 A1 | 11/2001 | Levinson et al. | |
| 2001/0044639 A1 | 11/2001 | Levinson | |
| 2002/0002401 A1 | 1/2002 | McGuckin, Jr. et al. | |
| 2002/0077658 A1 | 6/2002 | Ginn | |
| 2002/0082641 A1 | 6/2002 | Ginn et al. | |
| 2002/0107542 A1 | 8/2002 | Kanner et al. | |
| 2002/0151921 A1 | 10/2002 | Kanner et al. | |
| 2002/0169478 A1 | 11/2002 | Schwartz et al. | |
| 2002/0173820 A1 * | 11/2002 | Akerfeldt et al. | 606/225 |
| 2002/0188318 A1 | 12/2002 | Carley et al. | |
| 2002/0198562 A1 * | 12/2002 | Akerfeldt et al. | 606/213 |
| 2003/0093096 A1 | 5/2003 | McGuckin, Jr. et al. | |
| 2003/0109891 A1 * | 6/2003 | Dana et al. | 606/148 |
| 2003/0144695 A1 | 7/2003 | McGuckin, Jr. et al. | |
| 2003/0167062 A1 | 9/2003 | Gamabale et al. | |
| 2003/0195514 A1 | 10/2003 | Trieu et al. | |
| 2003/0199987 A1 | 10/2003 | Berg et al. | |
| 2004/0059350 A1 * | 3/2004 | Gordon et al. | 606/144 |
| 2004/0093024 A1 | 5/2004 | Lousararian et al. | |
| 2004/0122451 A1 * | 6/2004 | Wood | 606/148 |
| 2004/0225303 A1 * | 11/2004 | Dana et al. | 606/148 |
| 2005/0043746 A1 * | 2/2005 | Pollak et al. | 606/144 |
| 2005/0085851 A1 * | 4/2005 | Fiehler et al. | 606/213 |
| 2005/0085852 A1 * | 4/2005 | Ditter | 606/213 |
| 2005/0085853 A1 * | 4/2005 | Forsberg et al. | 606/213 |
| 2005/0085856 A1 * | 4/2005 | Ginn | 606/213 |
| 2005/0096697 A1 * | 5/2005 | Forsberg et al. | 606/213 |
| 2005/0107827 A1 * | 5/2005 | Paprocki | 606/228 |
| 2005/0149065 A1 * | 7/2005 | Modesitt | 606/144 |
| 2005/0205640 A1 | 9/2005 | Milliman | |
| 2006/0047314 A1 * | 3/2006 | Green | 606/232 |
| 2006/0190037 A1 | 8/2006 | Ginn et al. | |
| 2006/0235505 A1 | 10/2006 | Oepen et al. | |
| 2006/0241579 A1 | 10/2006 | Kawaura et al. | |
| 2006/0264977 A1 * | 11/2006 | Dana et al. | 606/148 |
| 2006/0265008 A1 | 11/2006 | Maruyama et al. | |
| 2006/0265010 A1 | 11/2006 | Paraschac et al. | |
| 2007/0010853 A1 | 1/2007 | Ginn et al. | |
| 2007/0060895 A1 * | 3/2007 | Sibbitt et al. | 604/215 |
| 2007/0149987 A1 * | 6/2007 | Wellman et al. | 606/148 |
| 2007/0255317 A1 | 11/2007 | Fanton et al. | |
| 2007/0260125 A1 | 11/2007 | Strauss et al. | |
| 2007/0270904 A1 | 11/2007 | Ginn | |
| 2007/0276433 A1 | 11/2007 | Huss | |
| 2008/0065151 A1 * | 3/2008 | Ginn | 606/213 |
| 2008/0065156 A1 * | 3/2008 | Hauser et al. | 606/232 |
| 2008/0114395 A1 * | 5/2008 | Mathisen et al. | 606/215 |
| 2009/0012537 A1 * | 1/2009 | Green | 606/139 |
| 2009/0069847 A1 * | 3/2009 | Hashiba et al. | 606/232 |
| 2009/0157102 A1 | 6/2009 | Reynolds et al. | |
| 2009/0248067 A1 * | 10/2009 | Maiorino | 606/228 |
| 2009/0254119 A1 * | 10/2009 | Sibbitt et al. | 606/213 |
| 2009/0306671 A1 | 12/2009 | McCormack et al. | |
| 2009/0306685 A1 * | 12/2009 | Fill | 606/148 |
| 2010/0042144 A1 * | 2/2010 | Bennett | 606/213 |
| 2010/0130965 A1 * | 5/2010 | Sibbitt et al. | 606/2 |
| 2010/0179589 A1 | 7/2010 | Roorda et al. | |
| 2010/0179590 A1 * | 7/2010 | Fortson et al. | 606/216 |
| 2010/0256670 A1 | 10/2010 | Ginn et al. | |
| 2011/0029012 A1 | 2/2011 | Tegels | |
| 2011/0106104 A1 * | 5/2011 | Dana et al. | 606/138 |
| 2011/0172702 A1 * | 7/2011 | Fiehler et al. | 606/213 |
| 2012/0059414 A1 * | 3/2012 | Roorda | 606/232 |
| 2012/0109189 A1 | 5/2012 | Voss et al. | |
| 2012/0184991 A1 | 7/2012 | Paraschac et al. | |
| 2012/0203328 A1 | 8/2012 | Yribarren | |
| 2012/0220833 A1 | 8/2012 | Ehrenreich | |
| 2013/0046331 A1 * | 2/2013 | Christensen et al. | 606/200 |
| 2013/0053884 A1 * | 2/2013 | Roorda | 606/232 |
| 2013/0103077 A1 * | 4/2013 | Ditter | 606/213 |
| 2013/0110165 A1 * | 5/2013 | Burkhart et al. | 606/232 |
| 2013/0218206 A1 * | 8/2013 | Gadlage | 606/232 |
| 2013/0231701 A1 * | 9/2013 | Voss et al. | 606/232 |
| 2013/0296887 A1 * | 11/2013 | Dana et al. | 606/138 |

(56) References Cited

U.S. PATENT DOCUMENTS

| | | | |
|---|---|---|---|
| 2013/0345745 A1* | 12/2013 | Kim | 606/225 |
| 2014/0039271 A1 | 2/2014 | Ehrenreich | |
| 2014/0148824 A1* | 5/2014 | Fujisaki et al. | 606/144 |
| 2014/0228868 A1* | 8/2014 | Hassan et al. | 606/153 |
| 2014/0336702 A1* | 11/2014 | Rowe et al. | 606/228 |
| 2014/0364904 A1* | 12/2014 | Kim | 606/228 |

OTHER PUBLICATIONS

U.S. Appl. No. 13/035,939, Jan. 31, 2013, Office Action.
U.S. Appl. No. 60/502,925, filed Sep. 15, 2003, Paraschac.
U.S. Appl. No. 10/941,693, Nov. 17, 2006, Office Action.
U.S. Appl. No. 10/941,693, May 7, 2007, Office Action.
U.S. Appl. No. 10/941,693, Dec. 31, 2007, Office Action.
U.S. Appl. No. 10/941,693, Jul. 9, 2008, Office Action.
U.S. Appl. No. 10/941,693, Mar. 2, 2009, Office Action.
U.S. Appl. No. 10/941,693, Oct. 23, 2009, Office Action.
U.S. Appl. No. 10/941,693, Sep. 28, 2011, Notice of Allowance.
U.S. Appl. No. 11/460,863, Jul. 12, 2007, Office Action.
U.S. Appl. No. 11/460,863, Feb. 5, 2008, Office Action.
U.S. Appl. No. 11/460,863, Oct. 10, 2008, Office Action.
U.S. Appl. No. 11/460,863, Apr. 13, 2009, Office Action.
U.S. Appl. No. 13/219,004, filed Aug. 26, 2011, Roorda.
U.S. Appl. No. 12/684,470, filed Jan. 8, 2010, Voss et al.
U.S. Appl. No. 12/917,195, Jun. 28, 2012, Office Action.
U.S. Appl. No. 12/917,195, Aug. 1, 2012, Office Action.
U.S. Appl. No. 13/022,246, May 11, 2012, Office Action.
U.S. Appl. No. 13/022,246, Jun. 7, 2013, Office Action.
U.S. Appl. No. 12/917,195, Aug. 7, 2013, Notice of Allowance.
U.S. Appl. No. 13/219,004, Aug. 9, 2013, Office Action.
U.S. Appl. No. 13/219,004, Dec. 19, 2012, Restriction Requirement.
U.S. Appl. No. 13/219,004, Feb. 14, 2013, Office Action.
U.S. Appl. No. 13/022,246, Nov. 28, 2012, Office Action.
U.S. Appl. No. 13/022,246, Nov. 14, 2013, Notice of Allowance.
U.S. Appl. No. 13/035,939, Sep. 10, 2013, Office Action.
U.S. Appl. No. 13/035,939, Apr. 10, 2014, Office Action.
U.S. Appl. No. 13/035,939, Aug. 21, 2014, Office Action.
U.S. Appl. No. 13/219,004, Aug. 5, 2014, Office Action.
U.S. Appl. No. 13/356,129, May 6, 2014, Office Action.
U.S. Appl. No. 13/356,129, Sep. 15, 2014, Office Action.
U.S. Appl. No. 14/052,658, Sep. 4, 2014, Office Action.
U.S. Appl. No. 13/035,939, Mar. 13, 2015, Office Action.
U.S. Appl. No. 13/219,004, Feb. 17, 2014, Notice of Allowance.
U.S. Appl. No. 13/356,129, Mar. 18, 2015, Office Action.
U.S. Appl. No. 14/052,658, Mar. 27, 2015, Office Action.

* cited by examiner

SUTURE SECURING SYSTEMS, DEVICES AND METHODS

BACKGROUND OF THE INVENTION

1. The Field of the Invention

Embodiments of the invention relate generally to medical systems, devices and methods. More particularly, embodiments of the invention relate to suture securing systems, devices and methods for closing holes in tissue.

2. The Relevant Technology

Sutures are used to sew tissue together, and thereby close tissue openings, cuts or incisions during or after any of a very wide variety of medical procedures. Typically, the surgeon manually ties together suture lengths to close the opening; however, there are a number of disadvantages of knotting sutures together to secure tissues to one another. For example, manual knot tying requires considerable dexterity. Also, manual knot tying can take considerable time. Knot tying is further complicated by the fact that surgical sutures have low friction surfaces. It is typically necessary for a surgeon to include many "throws" when tying the knot. Unfortunately, as the number of loops or "throws" incorporated into the knot increase, the knot becomes increasingly large and bulky. Moreover, the surgeon typically needs to handle strands of adequate suture length prior to commencing manual knot tying. Furthermore, manually tied knots often lock prior to reaching the intended amount of tension to be applied to the tissue. Thus, manual knot tying requires considerable space both in which to view, and to perform, the actual suture knot tying. Further still, many surgical procedures are moving away from being open and toward being minimally invasive wherein the procedure is performed within a small opening formed in a patient's tissue. Many times the surgeon cannot see the vessel which they are trying to close with the suture. After a manually tied knot has been advanced over a repair site and tightened, the excess suture must be cut away. Typically, a surgeon may utilize a scalpel or a pair of scissors to cut off the suture ends just below the exterior surface of the patient's skin. Many times a surgeon cannot easily shorten this cut length because the location of the knot is well below the patient's tissue and not readily accessible, therefore they can only shorten the suture to the point that they can visually see. This is problematic because leaving lengths of suture within the wound may lead to irritation of the incision. More significantly, a relatively long suture end, extending from the knot at the vessel repair to the skin level, may act as a "wick" for infective microorganisms which may be present at skin level. The wick could provide a conduit for these microorganisms to travel from the skin surface to the vessel repair, thereby leading to infection.

BRIEF SUMMARY OF THE INVENTION

An embodiment of a suture securing system is provided for use in closing a vessel puncture site while eliminating the need for suture lengths to be manually tied in knots. In one embodiment, a suture securing system may include an elongate body having a shaft and a barrel, a knot replacement element, a snare, and a trimmer member. The shaft may have a proximal end and a distal portion. The barrel may have a distal end comprising an opening and may be mounted on the shaft such that the shaft can slide relative to the barrel. The knot replacement element may have an outer surface and an inner lumen extending therethrough. The inner lumen of the knot replacement element can be configured to receive the suture lengths. The knot replacement element can be at least partially positioned within the distal end of the barrel adjacent to the distal portion of the shaft and be configured to selectively fasten the suture lengths together over the vessel repair site. The snare may have an elongate portion and a snare portion and be configured to draw the suture lengths through the inner lumen of the knot replacement element and at least a portion of the elongate body. Finally, the trimmer member may be configured to selectively trim the suture lengths extending proximal to the knot replacement element.

In another embodiment, a suture securing system may include a shaft, a barrel, a knot replacement element, a collet, a snare, and an actuator. The shaft can include a proximal end and a distal portion. The barrel can extend along at least a portion of the shaft and include a proximal end and a distal end. The barrel can also include one or more side ports and a flared portion. The knot replacement element may have an outer surface and an inner lumen extending therethrough. The inner lumen of the knot replacement element can be configured to receive the suture lengths. The knot replacement element can be at least partially positioned within the distal end of the barrel adjacent to the distal portion of the shaft and be configured to selectively fasten the suture lengths together over the vessel repair site. The snare can be configured to draw the suture lengths through the knot replacement element and out the out the one or more side ports of the barrel. The collet can be connected to the shaft and be disposed within the flared portion of the barrel. The collet may be moveable between a first position and a second position wherein the collet is forced together by an inner surface of the flared portion to fasten the knot replacement element onto the suture lengths. Finally, the actuator can be operatively connected to the collet and be configured to move the collet between the first position and the second position.

Embodiments are also directed to methods of securing and trimming suture lengths over a vessel repair site. In some embodiments, the methods described herein may follow delivery of suture lengths through body tissue or a vessel wall by a suture mediated closure device. Some exemplary suture mediated closure devices may found in co-pending U.S. patent application, application Ser. No. 12/684,470, filed Jan. 8, 2010, U.S. Pat. No. 5,417,699, U.S. Pat. No. 5,902,311, U.S. Pat. No. 6,136,010, and U.S. Pat. No. 7,001,400, the complete disclosure which is hereby incorporated herein by reference. In other embodiments, the methods described herein may follow delivery of suture lengths through body tissue or a vessel wall by other means including manual suturing.

In one embodiment, after suture lengths have been placed on opposing sides of a puncture in a vessel wall, a method for securing and trimming suture lengths may include positioning a distal portion of a shaft in proximity with a tissue tract. The shaft may be moveably disposed within a barrel. A knot replacement element can be positioned within a distal portion of the barrel adjacent the distal portion of the shaft. The suture lengths can then be attached to a snare that is extended through the knot replacement element and at least a portion of the barrel. The suture lengths can then be drawn through the knot replacement element and at least a portion of the barrel with the snare. The shaft and the knot replacement element can then be advanced toward an outer surface of the vessel wall. The suture lengths can then be tensioned to pull the puncture closed. After the puncture has been closed, the knot replacement element may be secured onto the suture lengths such that the suture lengths are substantially fixed relative to the vessel wall. Finally, the suture lengths extending proximal of the knot replacement element can be trimmed with a trimmer member.

In another embodiment, after suture lengths have been placed on opposing sides of a puncture and a guide wire is positioned within the puncture, a method for securing and trimming suture lengths may include positioning a distal portion of a shaft in proximity with a tissue tract. The shaft may be moveably disposed within a sheath. A knot replacement element may be positioned within a distal portion of the sheath adjacent the distal portion of the shaft. After the shaft and knot replacement element are in proximity with the tissue tract, external pressure may be applied to the vessel wall for temporary hemostatis and the guide wire may be drawn through at least a portion of the sheath. The suture lengths can then be secured to a snare that is extended through at least a portion of the sheath and the knot replacement element. With the suture lengths secured to the snare, a balloon catheter may then be advanced over the guide wire to position it within the puncture and the balloon catheter may be inflated. With the balloon catheter inflated, the external pressure to the vessel wall may be released. The snare may then be manipulated to draw the suture lengths proximally through the knot replacement element and at least a portion of the sheath. The sheath and the knot replacement element can be advanced to an outer surface of the vessel wall. The suture lengths can then be tensioned to pull the puncture closed. With the puncture closed, the knot replacement element can be secured onto the suture lengths such that the suture lengths are substantially fixed relative to the vessel wall. The balloon catheter can then be deflated and the balloon catheter and the guide wire can be removed from the substantially closed puncture. The suture lengths can be further tensioned and the knot replacement element can be further compressed to further close the puncture. Finally, the suture lengths extending proximal to the knot replacement element may be trimmed with a trimmer member associated with the sheath.

These and other advantages and features of the present invention will become more fully apparent from the following description and appended claims, or may be learned by the practice of the invention as set forth hereinafter.

BRIEF DESCRIPTION OF THE DRAWINGS

To further clarify at least some of the advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

As used herein, the term "distal" is generally defined as in the direction of the patient or away from a user of a device. In the context of a medical device intervention with or through a vessel wall, "distal" herein refers to the interior or the lumen side of the vessel wall. Conversely, "proximal" generally means away from the patient or toward the user. In the context of a medical device intervention with or through a vessel wall, "proximal" herein refers to the exterior or outer side of the vessel wall.

The term "hemostasis" is herein used to mean the arrest of bleeding or substantially blocking flow of blood outwardly from a vessel lumen while the vessel lumen is pressurized or sustaining physiological blood flow. This amount of blockage or occlusion to flow is further defined such that the blood loss which is experienced is less than an amount which would affect procedural methods or outcomes according to a physician user of a device of ordinary skill in the art. In other words, "hemostasis" is not intended to mean only "total hemostasis" such that there is a total lack of blood loss. Rather, the term is used to also mean "procedural hemostasis" as a relative term in its use among physicians of ordinary skill.

The term "suturing" is herein intended to include the process of joining two surfaces or edges together with a suture such as a thread of material (either polymeric or natural), gut, wire, or the like or so as to close an aperture, opening, or wound, or join tissues.

Referring to FIGS. 1A-3B, a suture securing system 10, which is suitable to secure and trim suture lengths over a repair site in body tissue or a puncture in a vessel wall, will be discussed. It will be appreciated that the system of the present invention can be readily adapted for use with punctures made to various hollow body organs and lumens, although it may be necessary to modify the dimensions and other particular aspects of the system to accommodate different usage environments.

Figure 1A:
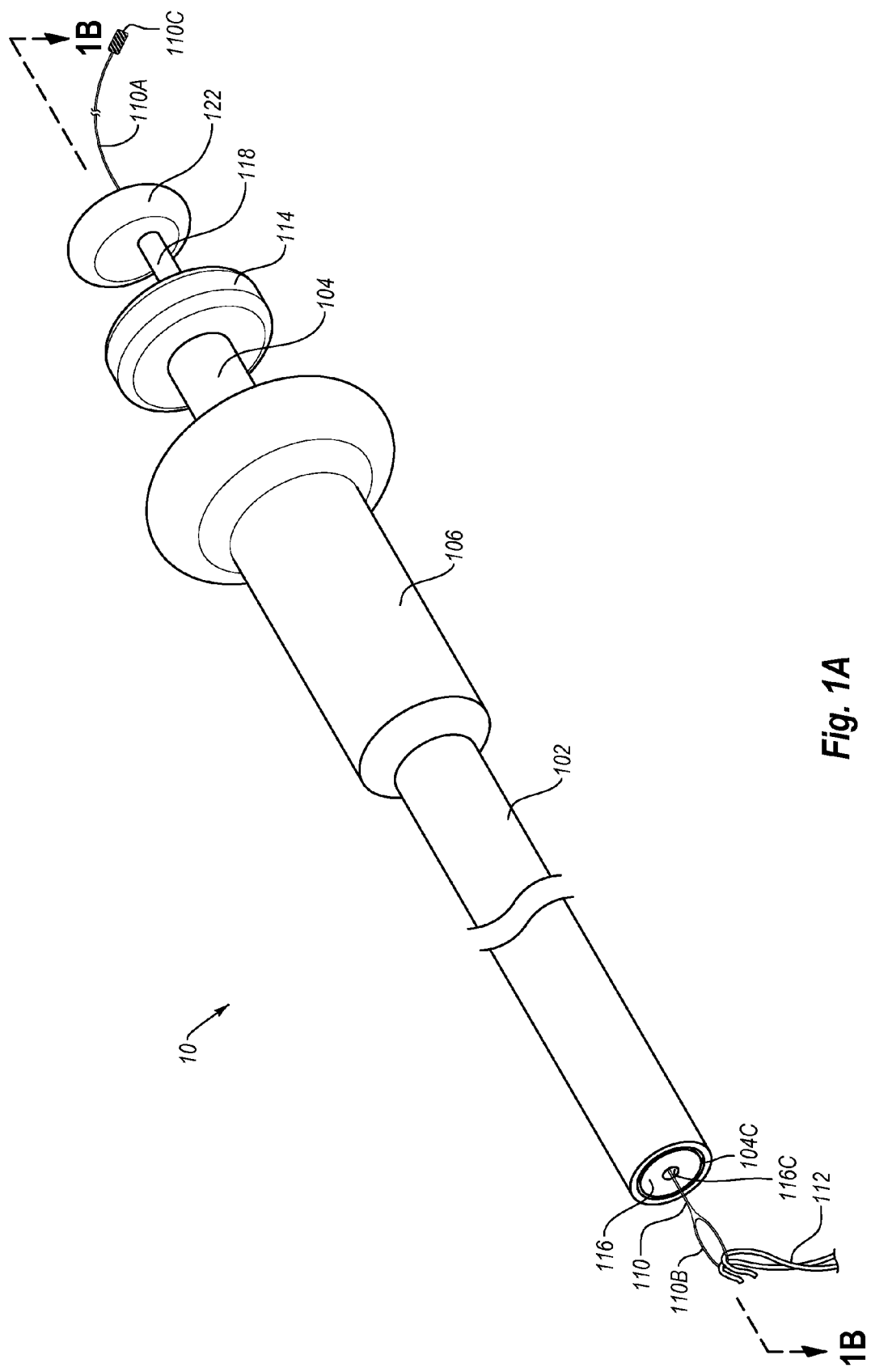
FIG. 1A illustrates a side perspective view of a suture securing system according to one example.

As shown in FIG. 1A, system 10 of the present invention comprises an elongate body which includes an outer barrel 102 and inner shaft 104. The barrel 102 can have a circular cross-sectional shape and include a grip portion 106 and an opening 104C at a distal end. While a barrel having a circular cross-sectional shape is shown, any cross-sectional shape that can be positioned over a repair site in body tissue is possible such as an oval, rectangular, triangular cross-sectional shape.

The shaft 104 can be sized, shaped, and configured to be slidably positioned within the barrel 102. The shaft 104 can include an access lumen 108 (shown in FIG. 1B) extending between a proximal end and a distal portion the shaft 104. The access lumen 108 can be configured to allow a snare 110 to be fed through the system 10 to facilitate manipulation of suture lengths 112, as described in detail hereinafter. The shaft 104 may have a handle 114 at the proximal end thereof and a knot replacement element 116 at the distal portion thereof. The knot replacement element 116 can be configured to tension and secure suture lengths 112 over a repair site 264 (shown in FIG. 2A) in a vessel wall 226 (shown in FIG. 2A) without having to tie a knot in the suture lengths 112. As shown, the knot replacement element 116 may be disposed at least partially within the barrel 102. In the illustrated embodiment, the knot replacement element 116 comprises a ring with an inner lumen 116C extending therethrough. At the proximal end of the shaft 104, the handle 114 can be used to eject the knot replacement element 116 from the distal end of the barrel 102.

The snare 110 can include a snare portion 110B for securing and tensioning the suture lengths 112 so that the suture lengths 112 may be drawn proximally through the knot replacement element 116 and proximally through the system 10 by the snare 110. As discussed below, pulling a control tab 110C of the snare 110 can cause the snare portion 110B to pull the suture lengths 112 through the inner lumen 116C of the knot replacement element 116, into the access lumen 108, and through the system 10. Manipulation of the snare 110 may be performed manually or any other suitable device and/or method may be used to manipulate the snare 110.

The snare portion 110B of the snare 110 may take any suitable form so long as it can engage or hold the suture lengths 112 so that the suture lengths 112 can be drawn up through the knot replacement element 116 and through at least a part of the system 10. For instance, the snare portion 110B may be a loop that is sized to receive the suture lengths 112. In another embodiment, the snare portion 110B may be malleable so that the snare portion 110B can be twisted onto the suture lengths 112. In other embodiments, the snare portion 110B may include barbs or friction elements that can frictionally engage the suture lengths 112.

The access lumen 108 (shown in FIG. 1B) of the shaft 104 may also be configured to receive a trimmer tube 118. The trimmer tube 118 may have a handle 122 at a proximal end thereof and a cutting element 118D at a distal end thereof (shown in FIG. 1B).

Figure 1B:
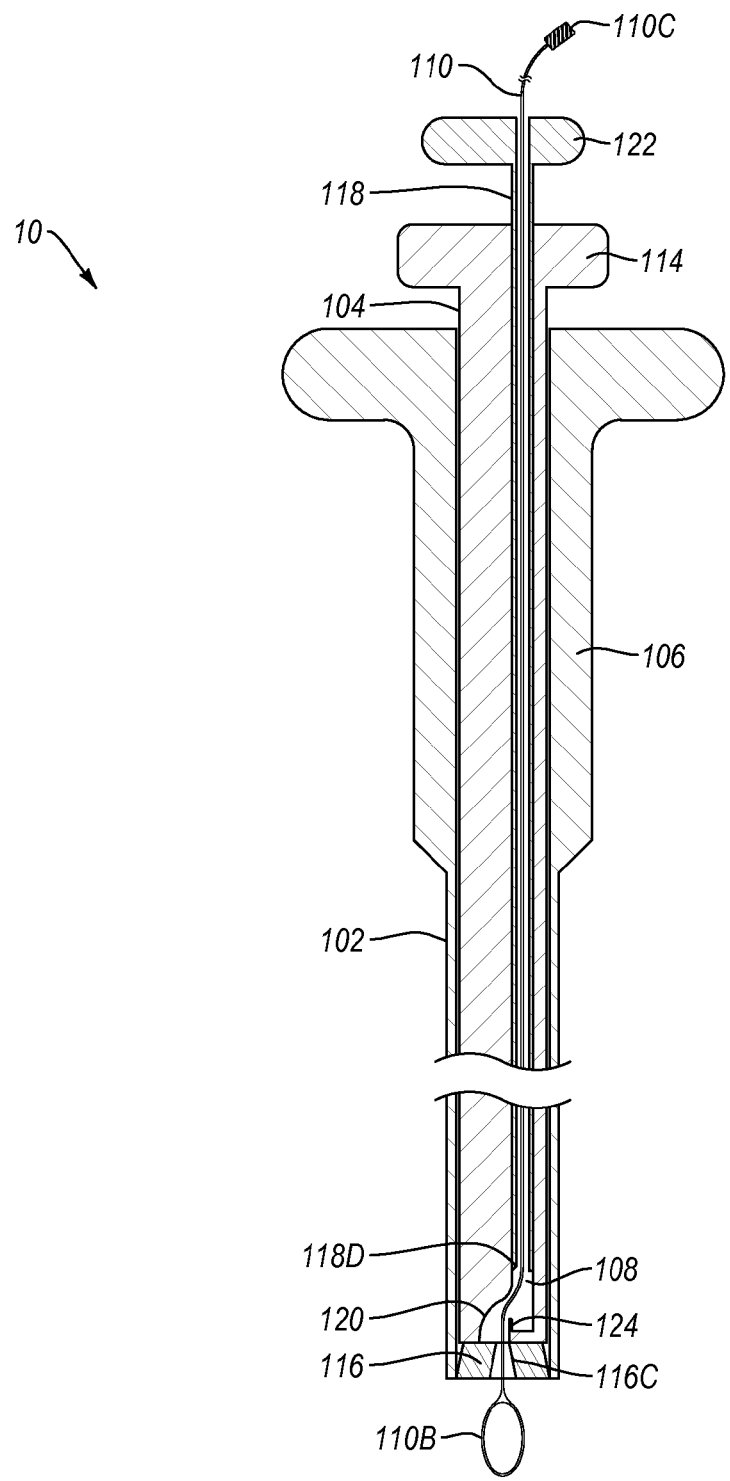
FIG. 1B illustrates a cross sectional view, taken along line 1B-1B of FIG. 1A, of the suture securing system shown in FIG. 1A.

Specific reference is now made to FIG. 1B which is a cross-sectional view of the system of FIG. 1A. The inner lumen 116C of the knot replacement element 116 may be configured to secure the suture lengths 112 together. In one embodiment, the inner lumen 116C may have a conical shape sized, shaped, and configured to function as a one-way stop such that the suture lengths 112 may move in the proximal direction relative to the knot replacement element 116 but not in the distal direction. Such a configuration permits a user to tension and secure the suture lengths 112 over the repair site 264 in the vessel wall 226 (shown in FIG. 2A) by drawing the suture lengths 112 through the inner lumen 116C of the knot replacement element 116 and the system 10, tensioning the suture lengths 112, and advancing the system 10 and the knot replacement element 116 over the sutures lengths 112 until the knot replacement element 116 reaches an outer surface of the vessel wall. Once the knot replacement element 116 reaches the vessel wall, the tensioned suture lengths 112 can move neither in the proximal or distal direction due to the configuration of the inner lumen 116C of the knot replacement element 116. While a ring-type knot replacement element is shown, any device that can secure the suture lengths over a repair site or puncture in body tissue is possible such as a tube, a spring, or a clip.

As shown in FIG. 1B, the system 10 also includes the trimmer tube 118 moveably mounted within the access lumen 108 of the shaft 104. In the illustrated embodiment, the trimmer tube 118 is hollow and elongated. The trimmer tube 118 can be configured to receive the suture lengths 112 (not shown) and the snare 110 as they are drawn through the inner lumen 116C of the knot replacement element 116 and into the access lumen 108 by a user. While the snare 110 is shown extending along a longitudinal axis of the system 10, the snare 110 may also extend out a side of the system 10. As an example, the barrel 102 may include side ports configured to allow the snare 110 to extend from a side wall of the barrel 102.

As shown in FIG. 1B, the longitudinal axis of the trimmer tube 118 can be offset relative to the inner lumen 116C of the knot replacement element 116. Such a configuration causes the suture lengths 112 to traverse a cutting element 118D of the trimmer tube 118 as the suture lengths 112 are drawn into the trimmer tube 118 from the inner lumen 116C of the knot replacement element 116 by a user. As shown, the shaft 104 may include a ramped surface 120 configured to guide the snare 110 and the suture lengths 112 across the cutting element 118D into the trimmer tube 118. The ramped surface 120 may include at least an elongate portion and curved portion. In one embodiment, the ramped surface 120 may include only a curved portion.

When the cutting element 118D is moved to a distal most position, the cutting element 118D can be positioned in the distal portion of the shaft 104. Advancing the handle 122 of the trimmer tube 118 distally can cause the cutting element 118D to cut, trim, or shear off suture lengths 112. The cutting element 118D may include a sharpened edge, a recessed razor blade, a serrated edge, or any other means suitable to sever the suture lengths 112. Optionally, the shaft 104 may include a backing element 124 configured to provide a stop, a shearing force, or backing for the cutting element 118D in the distal most position. The backing member 124 may comprise a block member, an elongate member, or any other member suitable to provide a stop, shearing force, or backing for the cutting element 118D. In other embodiments, the backing member 124 may be omitted. For example, the cutting portion 118D may sever the suture lengths 112 against the knot replacement element 116 or against tension formed in the suture lengths 112.

In another embodiment, the longitudinal axis of the trimmer tube 118 can be substantially aligned with the inner lumen 116C of the knot replacement element 116, but with a raised portion positioned therebetween such that the suture lengths 112 are routed around the raised portion in order to traverse the cutting element 118D of the trimmer tube 118.

FIGS. 2A-2D illustrate an exemplary method for tensioning and securing the suture lengths 112 over a vessel repair site 264 with the system 10. For ease of reference, only the distal portion of the system 10 is shown and described. The distal components may be manipulated by the proximal components in a similar manner as described above with reference to FIGS. 1A-1B.

Figure 2A:
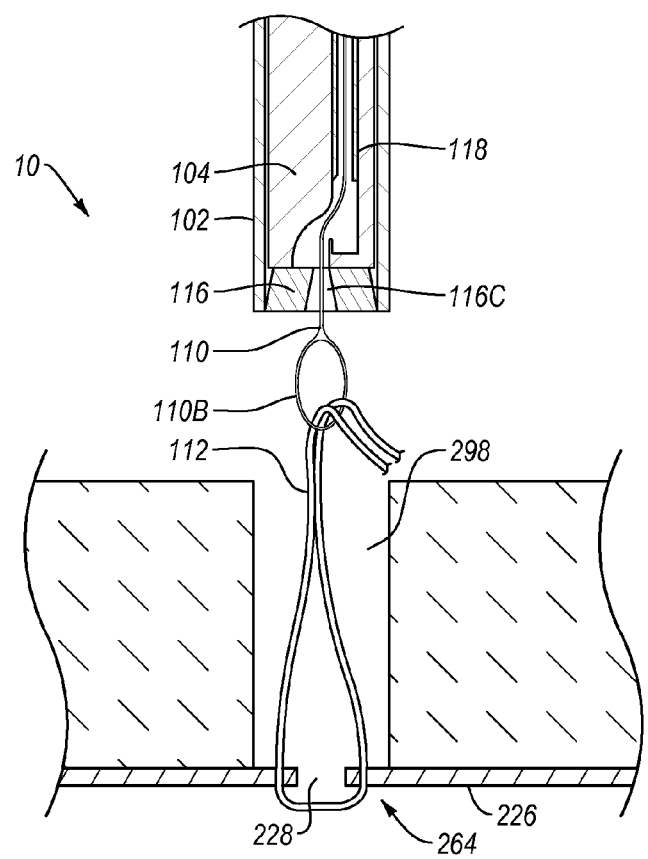
FIG. 2A is a partial cross sectional view illustrating an exemplary step in a method of securing suture lengths over a vessel repair site with the suture securing system shown in FIG. 1B.

Referring now to FIG. 2A, after the suture lengths 112 have been delivered through a vessel wall 226 on opposing sides of a puncture 228, the method can begin by positioning a distal portion of the barrel 102 in proximity with a tissue tract 298 at the vessel repair site 264 while the snare 110 is extended through the system 10 and the knot replacement element 116. The snare 110 may be sized, shaped and configured to move freely through the system 10, including the inner lumen 116C of the knot replacement element 116.

With the distal portion of the barrel 102 in proximity with the tissue tract 298 and the snare 110 extended through the system 10 and the knot replacement element 116, the suture lengths 112 can be fed through the snare portion 110B of the snare 110. The suture lengths 112 can then be secured to the snare 110 by twisting the snare portion 110B about the suture lengths 112, tying the suture lengths 112 onto the snare portion 110B, or any other means suitable to secure the suture lengths 112 to the snare 110.

Figure 2B:
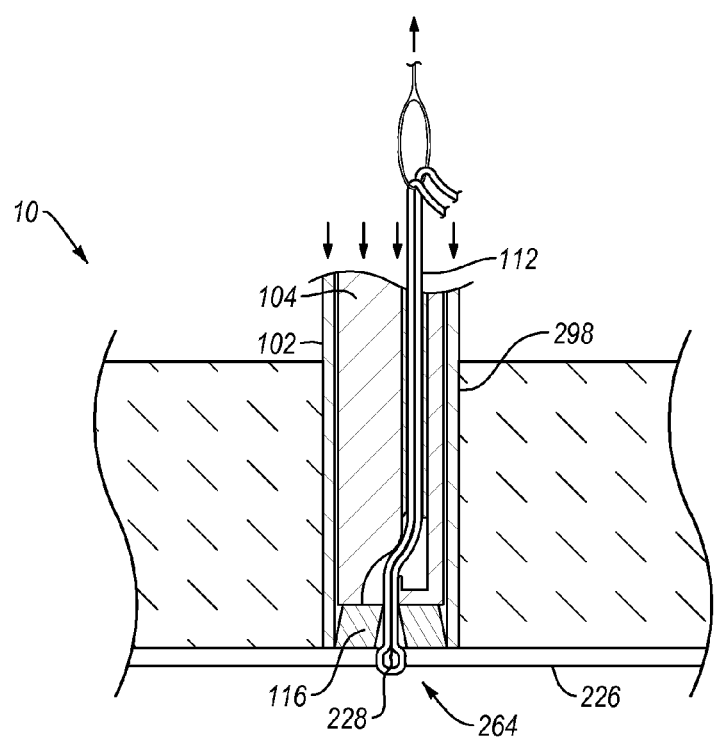
FIG. 2B is a partial cross sectional view illustrating an exemplary step in a method of securing suture lengths over a vessel repair site with the suture securing system shown in FIG. 1B.

As shown in FIG. 2B, the snare 110, along with the suture lengths 112, can then be drawn proximally through the system 10. As the snare 110 is pulled through the inner lumen 116C of the knot replacement element 116 and into the trimmer tube 118, the ramped surface 120 may guide the snare 110 into the trimmer tube 118. Once the suture lengths 112 have been drawn into the trimmer tube 118, the suture lengths 112 can be pulled by the snare 110 proximally out of the system 10 through the handle 122 (not shown) of the trimmer tube 118. The distal portion of the barrel 102 may then be advanced through the tissue tract 298 substantially to an outer surface of the vessel wall 226 as illustrated in FIG. 2B. Advancing the barrel 102 to the outer surface of the vessel wall 226, passes the knot replacement element 116 over the suture lengths 112 so that the knot replacement element 116 creates a one-way stop. The suture lengths 112 can then be tensioned to pull the puncture 228 closed, as shown. The suture lengths 112 may be tensioned with the snare 110, manually, or any other suitable means. With the knot replacement element 116 positioned over the closed puncture 228 and fastened onto the tensioned suture lengths, the suture lengths 412 can be considered secured over the vessel repair site 264.

Figure 2C:
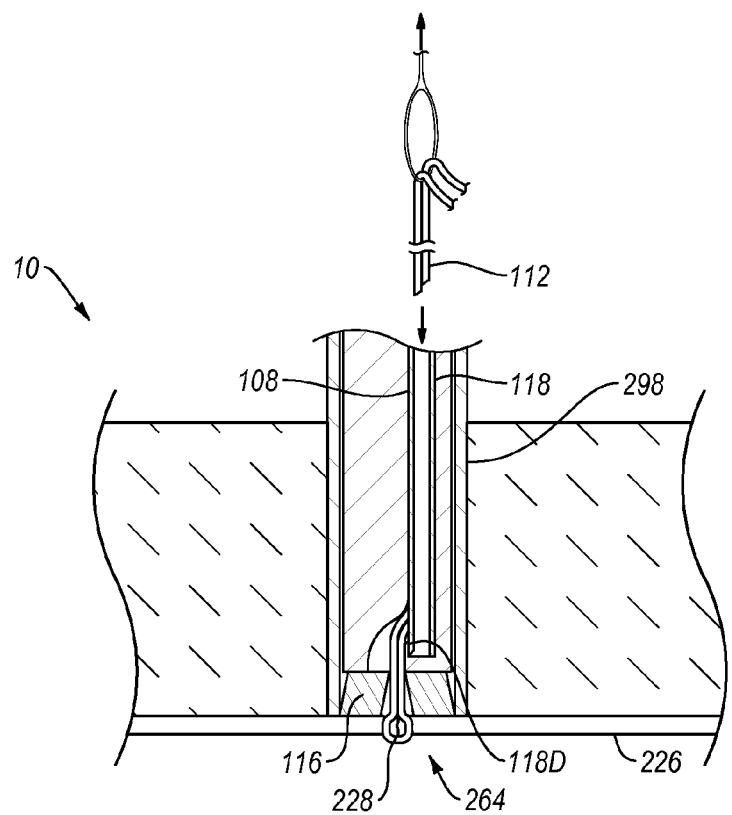
FIG. 2C is a partial cross sectional view illustrating an exemplary step in a method of securing suture lengths over a vessel repair site with the suture securing system shown in FIG. 1B.

As shown in FIG. 2C, with the tensioned suture lengths 112 secured over the closed puncture 228, the handle 122 (not shown) of the trimmer tube 118 can be advanced distally to extend the cutting element 118D of the trimmer tube 118 from the access lumen 108. Advancing the handle 122 of the trimmer tube 118 distally can cause the cutting element 118D to cut, trim, or shear off the suture lengths 112 extending proximally from the knot replacement element 116. Such a configuration allows the suture lengths 112 to be secured and trimmed well within tissue tract 298 of the vessel repair site 264. In addition, the suture lengths 112 remaining at the vessel repair site 264 are relatively close to the closed puncture 228 such that the suture lengths 112 do not function as a wick for infective microorganisms.

Figure 2D:
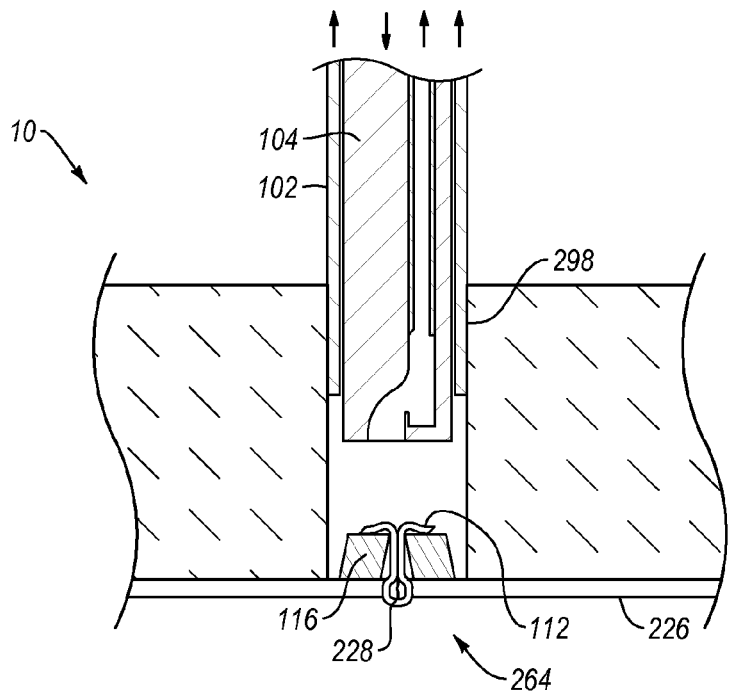
FIG. 2D is a partial cross sectional view illustrating an exemplary step in a method of securing suture lengths over a vessel repair site with the suture securing system shown in FIG. 1B.

As shown in FIG. 2D, the knot replacement element 116 can be ejected from the barrel 102 by the shaft 104 and the system 10 may be removed from the tissue tract 298. The knot replacement element 116 may then remained secured to the tensioned suture lengths 112 over the closed puncture 228 as shown.

Accordingly, as shown in FIGS. 2A-2D, the system 10 can be configured to tension and secure suture lengths over a vessel repair site, without tying a knot in the suture lengths.

Figure 3A:
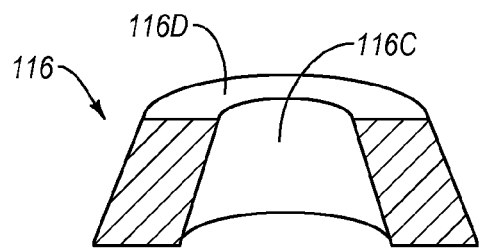
FIG. 3A is a cross sectional view of a knot replacement element according to one example.
Figure 3B:
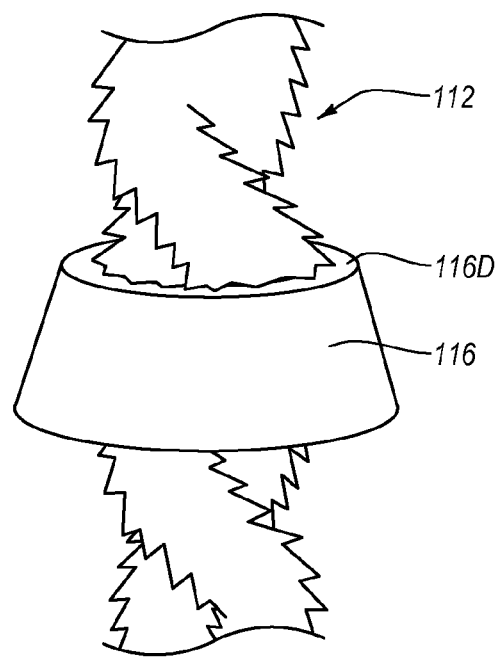
FIG. 3B illustrates the knot replacement element shown in FIG. 3A with suture lengths extending therethrough.

Referring to FIGS. 3A and 3B, the knot replacement element 116 can comprise a ring formed of magnesium, a bioabsorbable material, or any other material suitable to be deposited within a body. The knot replacement element 116 may include a proximal surface forming a locking edge 116D, a distal surface, and the inner lumen 116C extending between the proximal surface and the distal surface. The inner lumen 116C may be conical or tapered from the distal surface to the proximal surface. In one embodiment, the suture lengths 112 may comprise a monofilament suture having barbs or steps formed therein. The steps of the suture lengths 112 may be configured to help secure the suture lengths 112 over the closed puncture 228 by allowing the suture lengths 112 to proximally move through inner lumen 116C of the knot replacement element 116 but lock on the locking edge 116D of the knot replacement element 116 when a proximal force is applied to the knot replacement element 116.

Figure 3C:
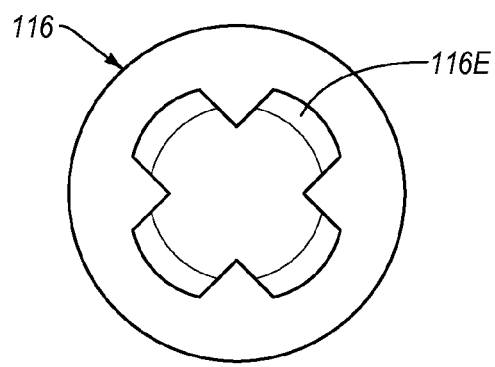
FIG. 3C is a top plan view of a knot replacement element according to another example.

In another embodiment shown in FIG. 3C, the knot replacement element 116 may comprise a ring having a cross-shaped inner lumen 116E extending therethrough as shown in FIG. 3B. The cross-shaped inner lumen 116E may help secure the suture lengths 112 over the closed puncture 228. For example, where the suture lengths 112 comprise a braided nylon suture and a proximal force is applied to the knot replacement element 116, the cross-shaped inner lumen 116E of the knot replacement element 116 may bunch, seize, and or knot up the braiding of the suture lengths 112 within the knot replacement element 116. In other embodiments, the cross-shaped inner lumen 116E may include friction elements to help secure the suture lengths 112 over the closed puncture 228 when the suture lengths 112 comprise a monofilament suture.

Referring to FIGS. 4A through 5D, a suture securing device 40 will be described according to an embodiment. The suture securing system 40 may be similar in many respects to the suture securing system 10 previously described above in FIGS. 1A-3B. To the extent features or components of this configuration function in a manner similar to that as described above, such disclosure is hereby incorporated into the following additional configuration. Like structures and/or components are given like reference numerals.

Figure 4A:
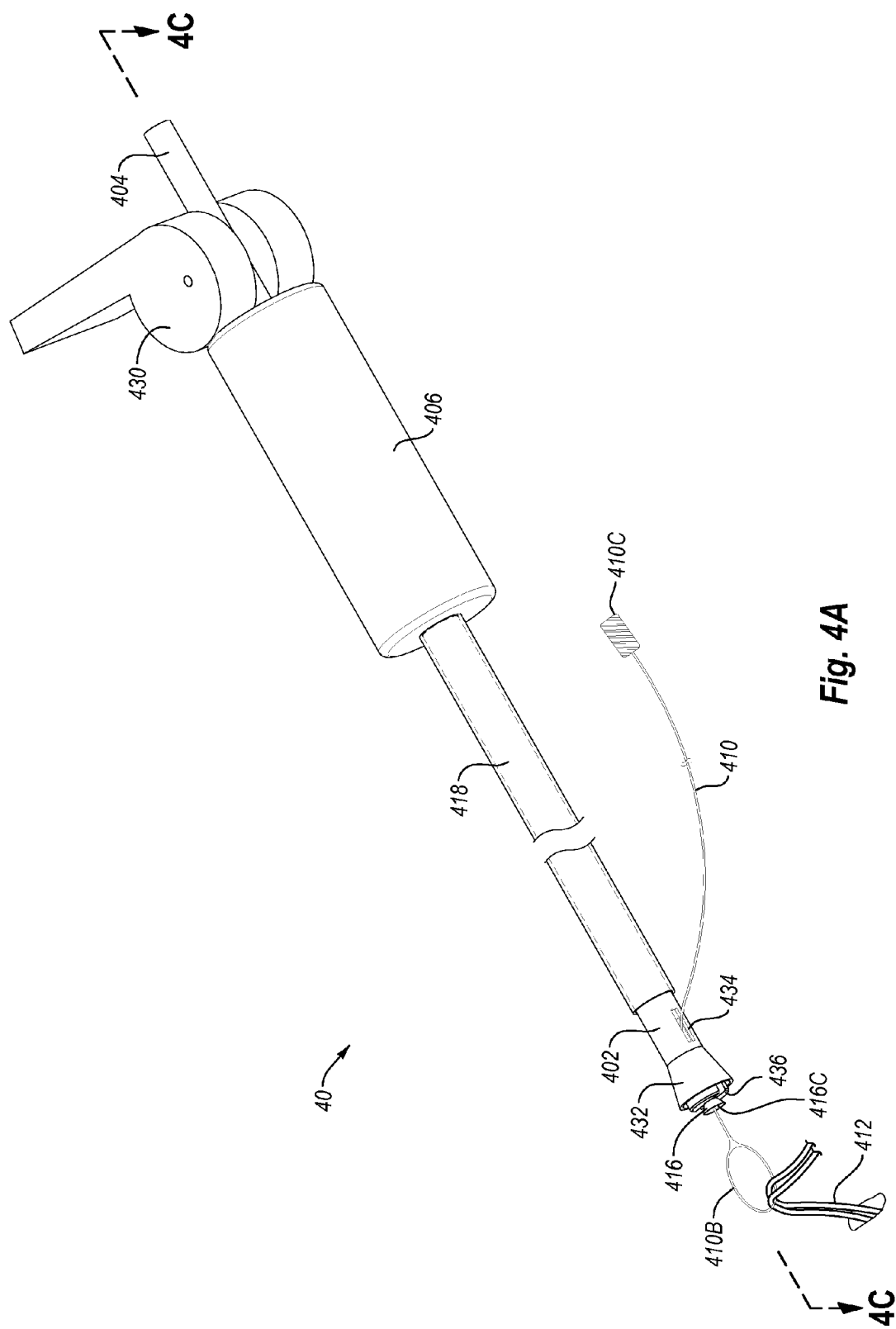
FIG. 4A illustrates a side perspective view of a suture securing system according to one example.
Figure 4B:
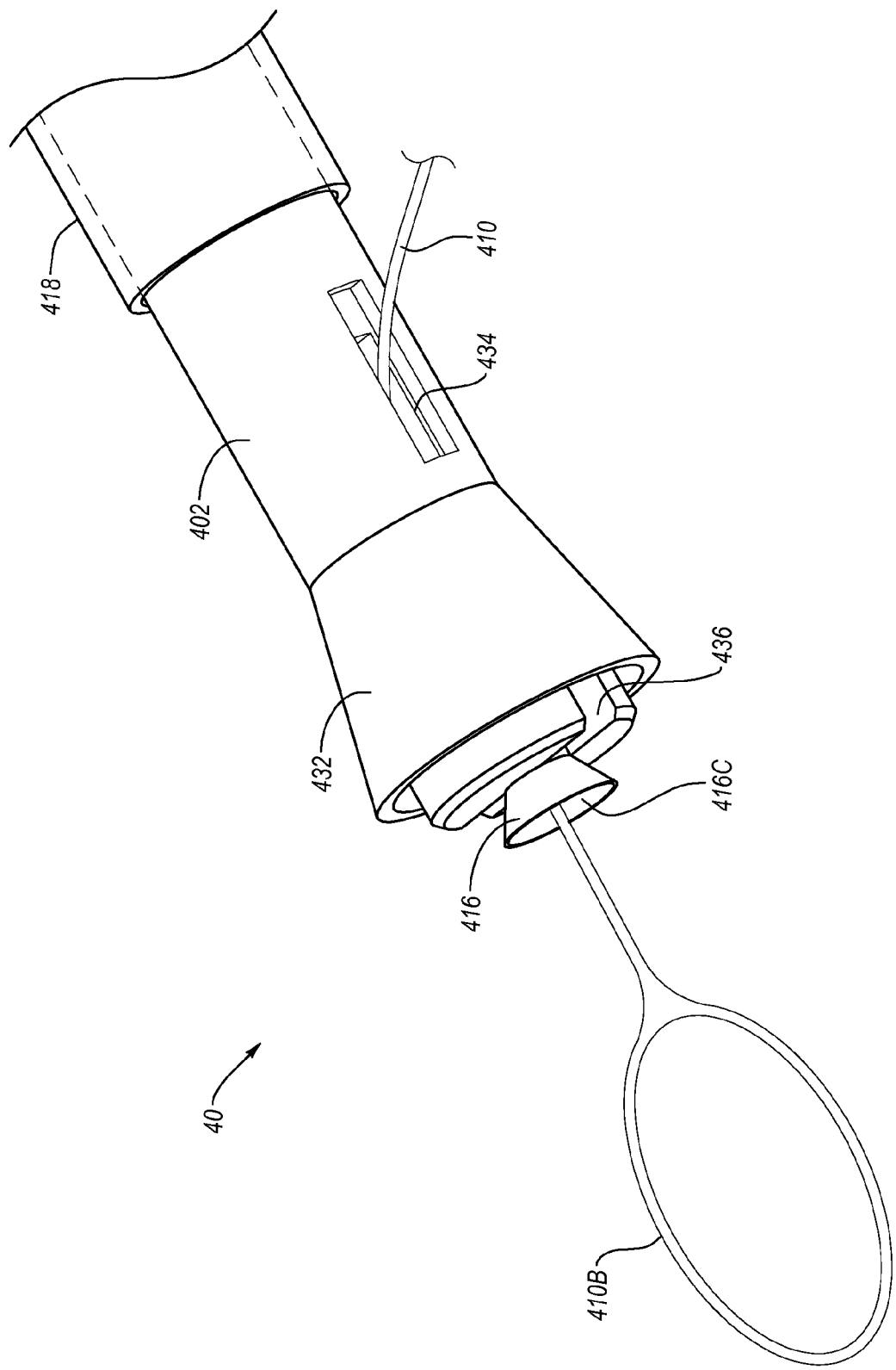
FIG. 4B illustrates a side perspective view of the distal portion of the suture securing system shown in FIG. 4A.

Referring now to FIGS. 4A and 4B, the system 40 may include an outer barrel 402, an inner shaft 404, a cam lever 430, a trimmer tube 418, a knot replacement element 416, and a snare 410. The barrel 402 may have a circular cross-sectional shape and include a grip portion 406 and a flared portion 432 at a distal end of the barrel 402. The barrel 402 may also include a side port 434 formed in a side wall of the barrel 402 that is in communication with the flared portion 432. Accordingly, the snare 410 can be drawn into the flared portion 432 and the knot replacement element 416 and out the side port 434 to pull suture lengths 412 through the system 40. While a circular barrel 402 is shown, any shape that can be positioned over a vessel repair site in body tissue is possible such as an oval, rectangular, or triangular shape.

The shaft 404 can be sized, shaped, and configured to be slidably positioned within the barrel 402. The shaft 404 may include the cam lever 430 at a proximal end and a collet 436 at a distal portion thereof. The collet 436 can be configured to selectively hold and mechanically crimp at least a portion of the knot replacement element 416. In the illustrated embodiment, the knot replacement element 416 is a tube-type element with an inner lumen 416C extending therethrough. At the proximal end of the shaft 404, the cam lever 430 can be rotated to pull the collet 436 up against the flared portion 432 of the barrel 402. Pulling the collet 436 proximally against the flared portion 432 can cause the collet 436 to compress on the knot replacement element 416 thereby crushing or mechanically crimping at least a portion of the knot replacement element 416 held within the collet 436. While actuation of the collet 436 is described with reference to the cam lever 430, any mechanism that can actuate the collet 436 is possible such as a plunger, a spring-loaded button, or a crank.

As shown, the trimmer tube 418 may be slidably attached to the barrel 402. The trimmer tube 418 may be configured to move between a retracted position wherein the trimmer tube 418 is positioned proximal to the side port 434 and an extended position wherein at least a portion of the trimmer tube 418 is positioned distal to the side port 434. In the extended position, the trimmer tube 418 may be configured to trim the suture lengths 412 protruding from the side port 434 of the barrel 402. The trimmer tube 418 may be actuated manually, by the cam lever 430, or by any other means suitable to move the trimmer tube 418 between the retracted position and the extended position. For example, an outer surface of the barrel 402 may include rifling configured to provide a track for the trimmer tube 418 such that rotation of the trimmer tube 418 by a user may move the trimmer tube 418 either proximally or distally along the length of the barrel 402. In another embodiment, the trimmer tube 418 may be slidably attached to the shaft 404 within the barrel 402. In another embodiment, the trimmer tube 418 may be attached to a header slidably attached to the barrel 402. A push rod may extend between the header and the cam lever 430 such that rotation of the cam lever 430 causes the push rod to operatively push the trimmer tube 418 into the extended position. The trimmer tube 418 may include a sharpened edge, a recessed razor blade, a serrated edge, or any other means suitable to sever the suture lengths 412.

The snare 410 may include a snare portion 410B for securing and/or tensioning the suture lengths 412 so that the suture lengths 412 may be drawn proximally through the knot replacement element 416 and out the side port 434 of the barrel 402. As discussed below, pulling a control tab 410C of the snare 410 proximally can cause the snare portion 410B to pull the suture lengths 412 proximally through the inner lumen 416C of the knot replacement element 416, into the flared portion 432 of the barrel 402, and out the side port 434. Manipulation of the snare 410 may be performed manually or with any other suitable device and/or method.

Figure 4C:
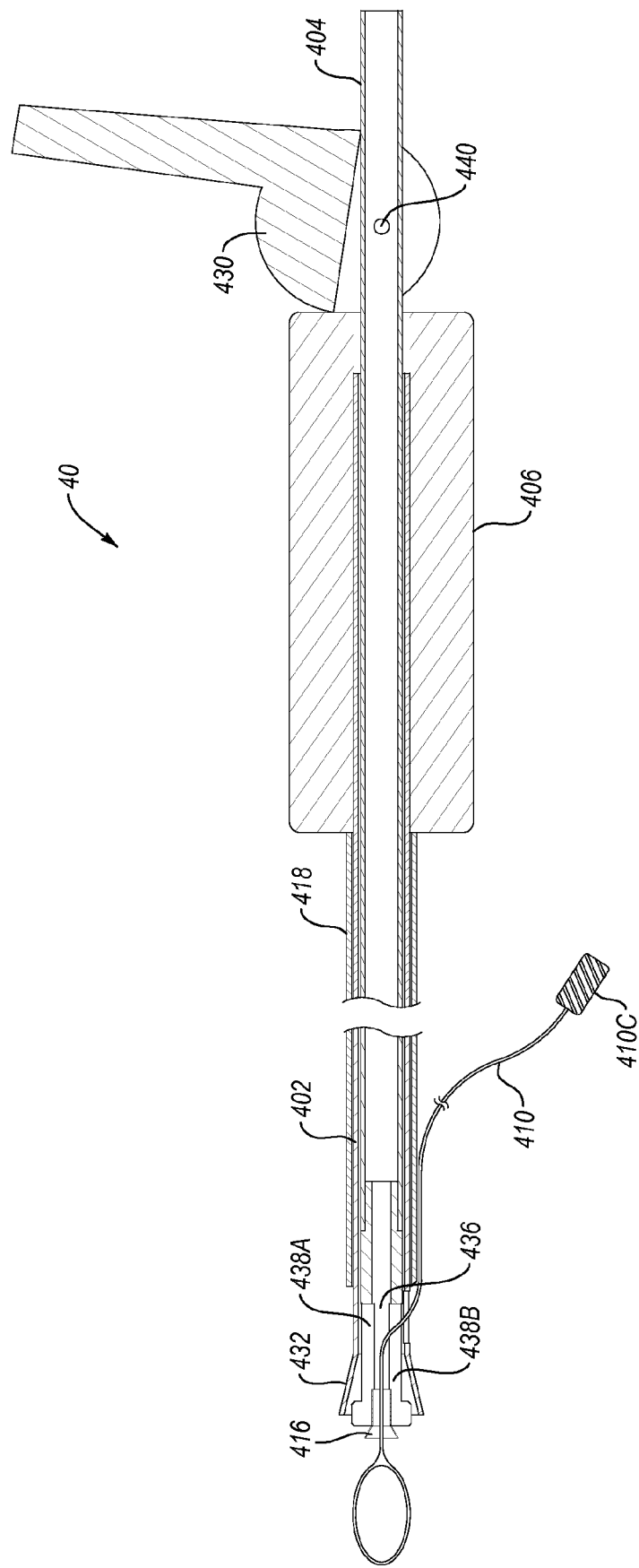
FIG. 4C illustrates a cross sectional view, taken along line 4C-4C of FIG. 4A, of the suture securing system shown in FIG. 4A.

Specific reference is now made to FIG. 4C which illustrates a cross sectional view, taken along line 4C-4C of FIG. 4A, of the system 40. Optionally, the shaft 404 may be hollow such that a user may advance and/or draw a procedural guide wire, the suture lengths 412 (shown in FIG. 5A), or other components along a longitudinal axis of the system 40 via the shaft 404. The collet 436 may comprise a pair of elongate members 438A, 438B, separated by a gap and attached to the distal portion of the shaft 404. In one embodiment, the pair of elongate members 438A, 438B may be integrally formed on the distal portion of the shaft 404. Each of the elongate members 438A, 438B may include a semi-cylindrical portion having chamfered edges (shown in FIG. 4B). The elongate members 438A, 438B may be formed of a resilient or flexible material such that the elongate members 438A, 438B may flex about a pivot point formed at or near the connection the elongate members 438A, 438B to the shaft 404. Such a configuration allows the collet 436 to expand and compress as the elongate members 438A, 438B move toward and away from each other. In another embodiment, the elongate members 438A, 438B may be slidably attached to a track extending across a diameter of the barrel 402. The elongate members 438A, 438B may slide across the track to move toward and away from each other. The gap in the collet 436 may be sized and configured to selectively hold the knot replacement element 416. When the shaft 404 is moved proximally by the cam lever 430, the collet 436 may compress as the elongate members 438A, 438B are forced together by the decreasing diameter of the flared portion 432 of the barrel 402. When the shaft 404 moves distally, the collet 436 may expand as the elongate members 438A, 438B move away from each other with the increasing diameter of the flared portion 432 of the barrel 402. While the elongate members 438A, 438B are described as moving relative to the flared portion 432 of the barrel 402, the system 40 may be configured such that the flare portion 432 moves relative to the elongate members 438A, 438B or both the elongate members 438A, 438B and the flared portion 432 may move simultaneously to force the elongate members 438A, 438B together. Forcing the elongate members 438A, 438B together with the flared portion 432 may cause the collet 436 to crush or mechanically crimp the knot replacement element 416 about the suture lengths 412. Although the collet 436 is shown including the elongate members 438A, 438B having the semi-cylindrical portions, any mechanism that can hold and crimp the knot replacement element is possible such as a conical sleeve having one or more slits along its length or a plurality of tapered blocks held in a circular position by a flexible medium. Furthermore, while a tube-type knot replacement element is shown, any device that can be secured onto the suture lengths is possible such as a ring, a spring, or a clip.

As shown in FIG. 4C, the cam lever 430 may be pivotally attached to the shaft 404 by a pivot pin 440. The cam lever 430 may include a lever portion and an eccentric wheel that produces proximal movement in the shaft 404 by striking against the grip portion 406 of the barrel 402 at one or more points on the rotational path of the cam lever 430. In another embodiment, the cam lever 430 may be a plate cam, a drum cam, a slidable button, a handle, or any other actuator configured to move the shaft 404 linearly to actuate the collet 436.

FIGS. 5A-5D illustrate an exemplary method for tensioning and securing the suture lengths 412 over a vessel repair site 464 with the system 40. For ease of reference, only the distal portion of the system 40 is shown and described. The distal components may be manipulated by the proximal components in a similar manner as described above with reference to FIGS. 4A-4C.

Figure 5A:
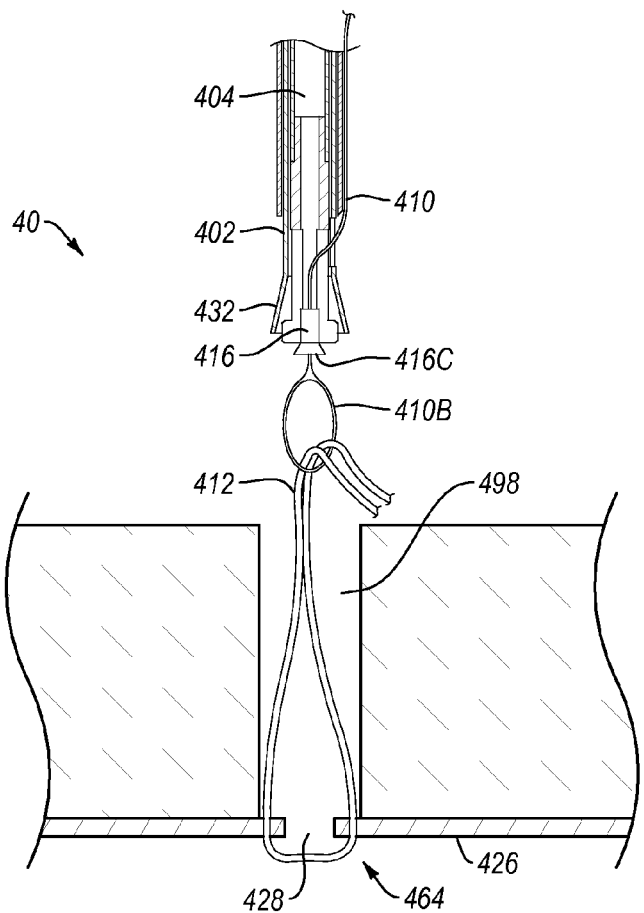
FIG. 5A is a partial cross sectional view illustrating an exemplary step in a method of securing suture lengths over a vessel repair site with the suture securing system shown in FIG. 4C.

Referring now to FIG. 5A, once the suture lengths 412 have been delivered through a vessel wall 426 on opposing sides of the puncture 428 by a suture mediated closure device, the method can begin by positioning the flared portion 432 of the barrel 402 in proximity with a tissue tract 498 at the vessel repair site 464 while the snare 410 is extended through the system 40 and the knot replacement element 416. The snare 410 may be sized, shaped and configured to move freely through the system 40, including the inner lumen 416C of the knot replacement device 416.

With the flared portion 432 of the barrel 402 and the snare 410 in proximity with the tissue tract 498, the suture lengths 412 can be fed through the snare portion 410B of the snare 410. The suture lengths 412 can then be secured to the snare 410 by twisting the snare portion 410B about the suture lengths 412, tying the suture lengths 412 onto the snare portion 410B, or any other means suitable to secure the suture lengths 412 to the snare 410.

Figure 5B:
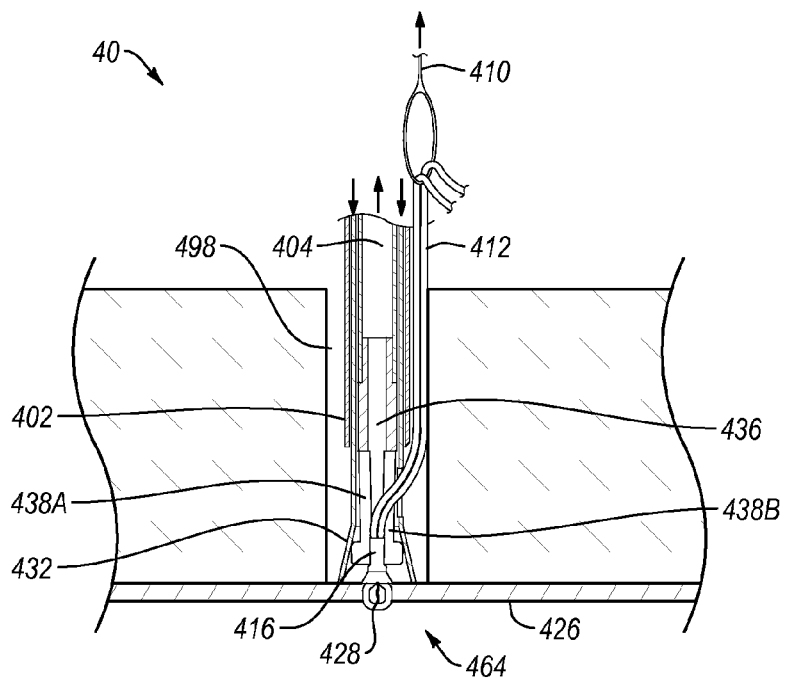
FIG. 5B is a partial cross sectional view illustrating an exemplary step in a method of securing suture lengths over a vessel repair site with the suture securing system shown in FIG. 4C.

Referring now to FIG. 5B, the snare 410, along with the suture lengths 412, can then be drawn proximally through the knot replacement element 416, into the barrel 402, and out of the side port 434 of the barrel 402. Once the suture lengths 412 have been pulled out of the side port 434, the flared portion 432 of the barrel 402 and the knot replacement element 416 may be advanced toward an outer surface of the vessel wall 426. Advancing the barrel 402 to the outer surface of the vessel wall 426, passes the knot replacement element 416 over the suture lengths 412. The suture lengths 412 may then be tensioned to pull the puncture 428 closed, as shown. The suture lengths 412 may be tensioned with the snare 410, manually, or by any other suitable means.

As illustrated in FIG. 5B, once the knot replacement element 416 is positioned over the outer surface of the vessel wall 426 and the puncture 438 is closed by the tensioned suture lengths 412, the cam lever 430 (shown in FIG. 4A) can be rotated to cause the collet 436 to mechanically crimp the knot replacement element 416 onto the suture lengths 412. Specifically, the cam lever 430 can be rotated to pull the shaft 404 in the proximal direction such that the elongate members 438A, 438B of the collet 436 are forced or compressed together by the flared portion 432 of the barrel 402. The compression of the elongate members 438A, 438B can mechanically crimp, crush, or compress the knot replacement element 416 onto the suture lengths 412. With the knot replacement element 416 crimped or fastened onto the tensioned suture lengths 412, the suture lengths 412 can be considered secured over the vessel repair site 464.

Figure 5C:
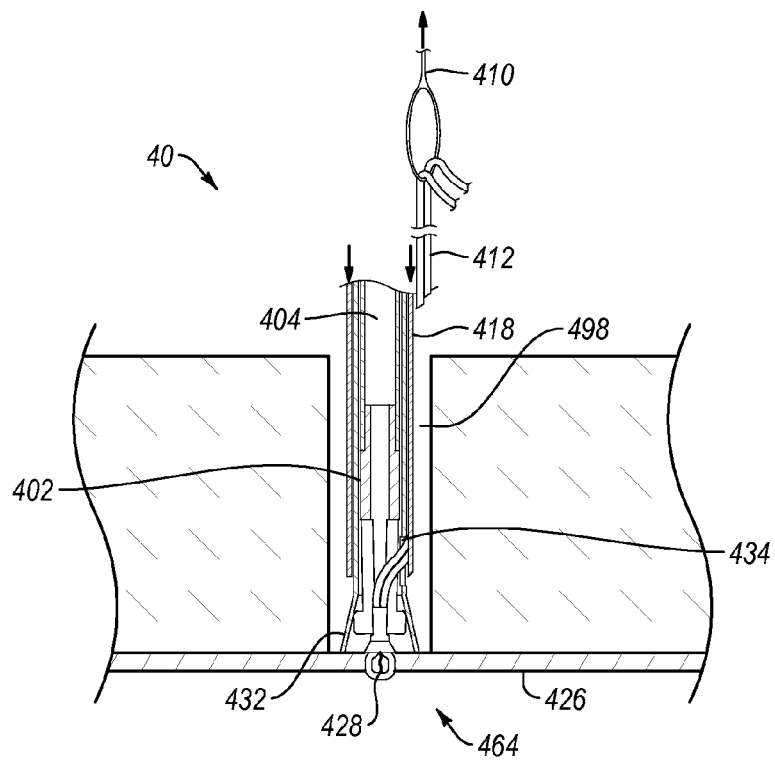
FIG. 5C is a partial cross sectional view illustrating an exemplary step in a method of securing suture lengths over a vessel repair site with the suture securing system shown in FIG. 4C.

As shown in FIG. 5C, with the suture lengths 412 secured, the trimmer tube 418 can be advanced into the extended position to trim the suture lengths 412 extending from the side port 434 of the barrel 402. Such a configuration of the system 40 allows the suture lengths 412 to be trimmed relatively close the closed puncture 428 at the vessel repair site 464 thereby reducing the risk of infection.

Figure 5D:
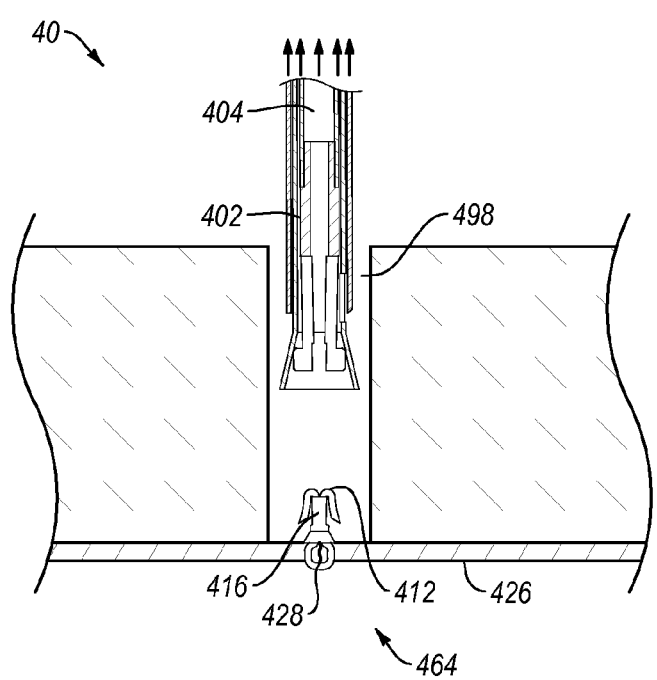
FIG. 5D is a partial cross sectional view illustrating an exemplary step in a method of securing suture lengths over a vessel repair site with the suture securing system shown in FIG. 4C.

As shown in FIG. 5D, the barrel 102 and the shaft 104 may be removed from the tissue tract 498 leaving the knot replacement element 416 secured onto the suture lengths 412 over the closed puncture 228. Accordingly, as shown in FIGS. 5A-5D, the system 40 can be configured to tension and secure suture lengths over a vessel repair site, without tying a knot in the suture lengths.

Referring to FIGS. 6A through 7G, a suture securing device 60 will be described according to an embodiment. The suture securing system 60 may be similar in many respects to the suture securing systems 10 and 40 previously described above in FIGS. 1A-5D. To the extent features or components of this configuration function in a manner similar to that as described above, such disclosure is hereby incorporated into the following additional configuration. Like structures and/or components are given like reference numerals.

Figure 6A:
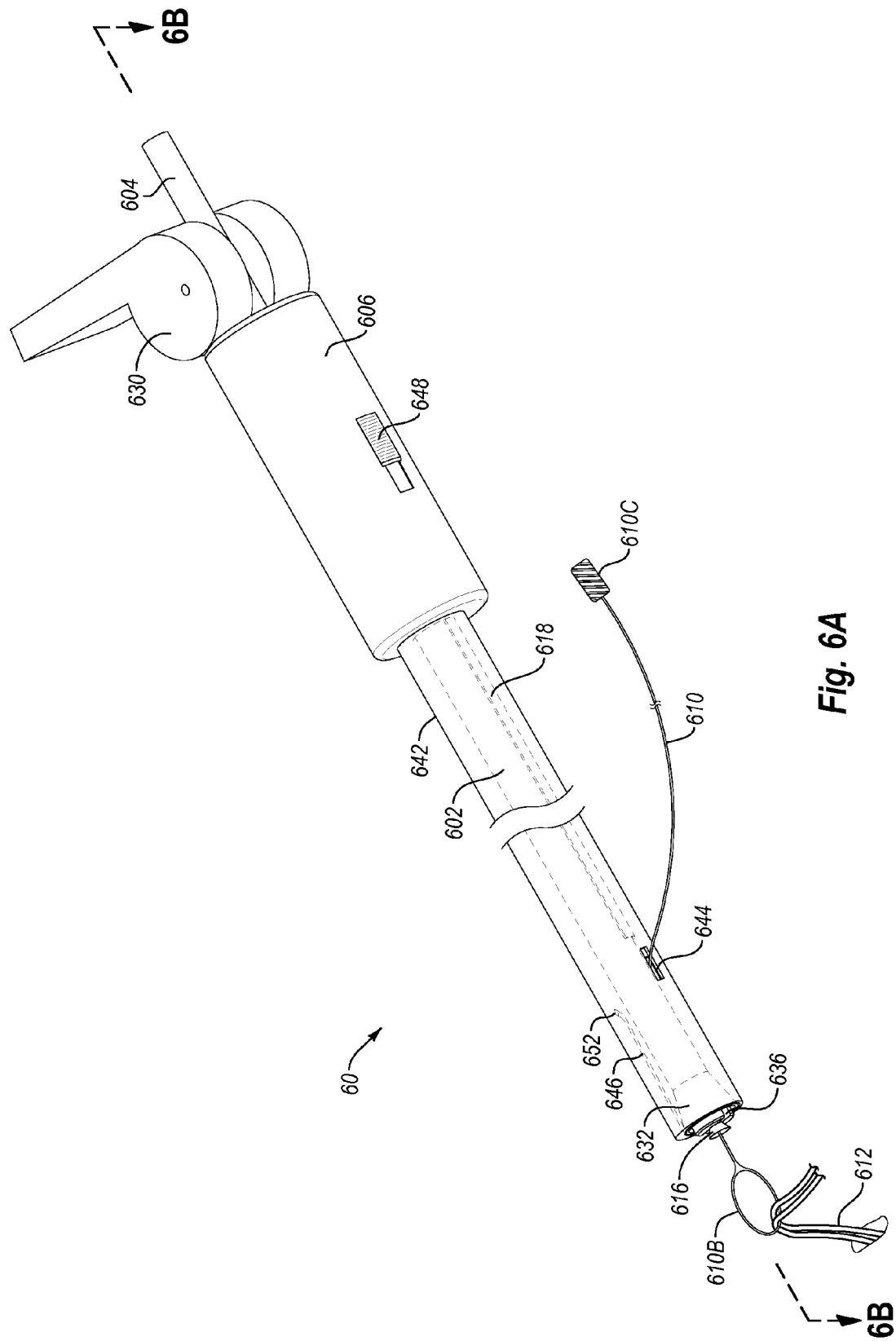
FIG. 6A illustrates a side perspective view of a suture securing system according to one example.

Referring now to FIG. 6A, the system 60 may include a grip portion 606, an outer sheath 642, barrel 602, an inner shaft 604, a cam lever 630, a trimmer member 618, a knot replacement element 616, and a snare 610. The sheath 642 may be attached to the grip portion 606 and substantially extend along the length of the barrel 602. The sheath 642 may include a side port 644 and a side lumen 646. The side lumen 646 may be sized, shaped and configured to allow a procedural guide wire or balloon catheter to pass between a second side port 652 of the sheath 642 and a distal end of the sheath 642 comprising an opening. The barrel 602 may comprise a tube having a flared portion 632 at a distal end. The barrel 602 may include a side port 634 (shown in FIG. 6B) formed in a side wall of the barrel 602 that is in communication with the flared portion 632 and the side port 644 of the sheath 642. Accordingly, the snare 610 may be drawn into the flared portion 632 of the barrel 602, through the side port 634 of the barrel 602, and out the side ports 644 of the sheath 642 to pull suture lengths 612 through the system 60. The barrel 602 and the sheath 642 may have a circular cross-sectional shapes, oval, rectangular, triangular, or any other cross-sectional shape suitable to position the system 60 over a puncture in a vessel wall.

The shaft 604 may be sized, shaped, and configured to be slidably positioned within the barrel 602. The shaft 604 may include a cam lever 630 at a proximal end and a collet 636 at a distal portion thereof. The collet 636 may be configured to selectively hold and mechanically crimp at least a portion of the knot replacement element 616. Again, the knot replacement element 616 may comprise a tube, a ring, a spring, a clip, or any other structure capable of securing the suture lengths 612 over a closed puncture. Furthermore, the cam lever 630 or any other suitable actuator such as a spring-loaded button or handle may be configured to actuate the collet 636.

As shown in FIG. 6A, the trimmer member 618 may be slidably attached to the barrel 602. The trimmer member 618 may be configured to selectively trim suture lengths 612 which have been drawn through the side port 644 of the sheath 642. In the illustrated embodiment, the trimmer member 618 is operatively connected to a spring-loaded button 648. The trimmer member 618 may include a sharpened edge, a recessed razor blade, a serrated edge, or any other means suitable to sever the suture lengths 612. The snare 610 may include a snare portion 610B and a control tab 610C and be configured to secure and/or tension the suture lengths 618. The snare 610 may be further be configured to draw the suture lengths 612 proximally through the knot replacement element 616 and out the side port 644 of the sheath 642.

Figure 6B:
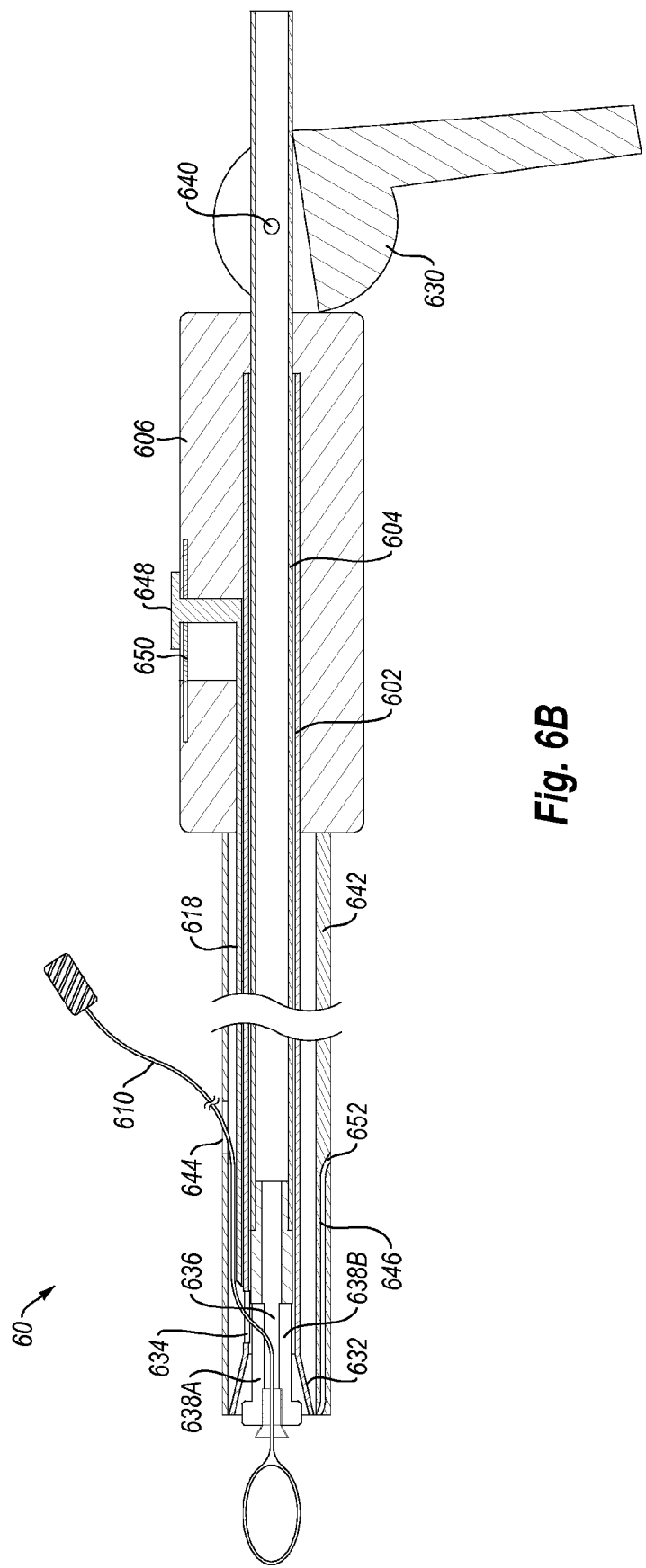
FIG. 6B illustrates a cross sectional view, taken along line 6B-6B of FIG. 6A, of the suture securing system shown in FIG. 6A.

Specific reference is now made to FIG. 6B which illustrates a cross sectional view, taken along line 6B-6B of FIG. 6A, of the system 60. As shown, the trimmer member 618 may extend along a length of the barrel 602 and a portion of the grip portion 606. The trimmer tube 618 may include a distal end having a sharpened edge, a recessed razor blade, a serrated edge, or any other means configured to selectively trim the suture lengths 612. The trimmer member 618 may be moveable between a retracted position wherein the distal end of the trimmer member 618 is proximal to the side port 634 of the barrel 602 and an extended position wherein the distal end of the trimmer member 618 is distal of the side port 634 of the barrel 602. The spring-loaded button 648 may be attached to a proximal end of the trimmer member 618. The spring-loaded button 648 may be positioned within a recess formed in the grip portion 606 and include a resilient element 650 configured to bias the trimmer member 618 in the retracted position. Such a configuration allows a user to push on the spring-loaded button 648 to move the trimmer member 618 into the extended position. When the user releases the spring-loaded button 648, the resilient element 650 can bias the trimmer member 618 back into the retracted position.

As shown in FIG. 6B, an inner diameter of the sheath 642 may be substantially equivalent to the largest diameter of the flared portion 632 of the barrel 602. Such a configuration creates a gap between the barrel 602 and the sheath 642 such that the snare 610 and suture lengths 612 may pass between the side port 634 of the barrel 602 and the side port 644 of the sheath 642. The side port 634 and the side port 644 may be aligned or unaligned. Still referring to FIG. 6B, the side lumen 646 of the sheath 642 may extend between an opening at a distal end of the sheath 642 and a second side port 652 of the sheath 642. As discussed above, the side lumen 646 may be formed in the sidewall of the sheath 642 and be configured to allow a user to advance and retract the procedural guide wire or the balloon catheter through a puncture 628 (shown in FIG. 7A). In another embodiment, the system 60 may not include a side lumen 646. For example, rather than the side lumen 646, the second side port 652 of the sheath 642 may be in communication with the gap formed between the inner diameter of the sheath 642 and the largest diameter of the flared portion 632. Such a configuration allows a user to pass the procedural guide wire or balloon catheter between the sheath 642 and the flared portion 632 to access the puncture 628. Similar to the system 40, the cam lever 630 may be pivotally attached to the shaft 404 by a pivot pin 640 and the collet 636 may include a pair of elongate members 638A, 638B, each having a semi-cylindrical portion with chamfered edges.

FIGS. 7A-7G illustrate an exemplary method for tensioning and securing the suture lengths 612 over a vessel repair site 664 with the system 60. For ease of reference, only the distal portion of the system 60 is shown and described. The distal components may be manipulated by the proximal components in a similar manner as described above with references to FIGS. 6A-6B.

Figure 7A:
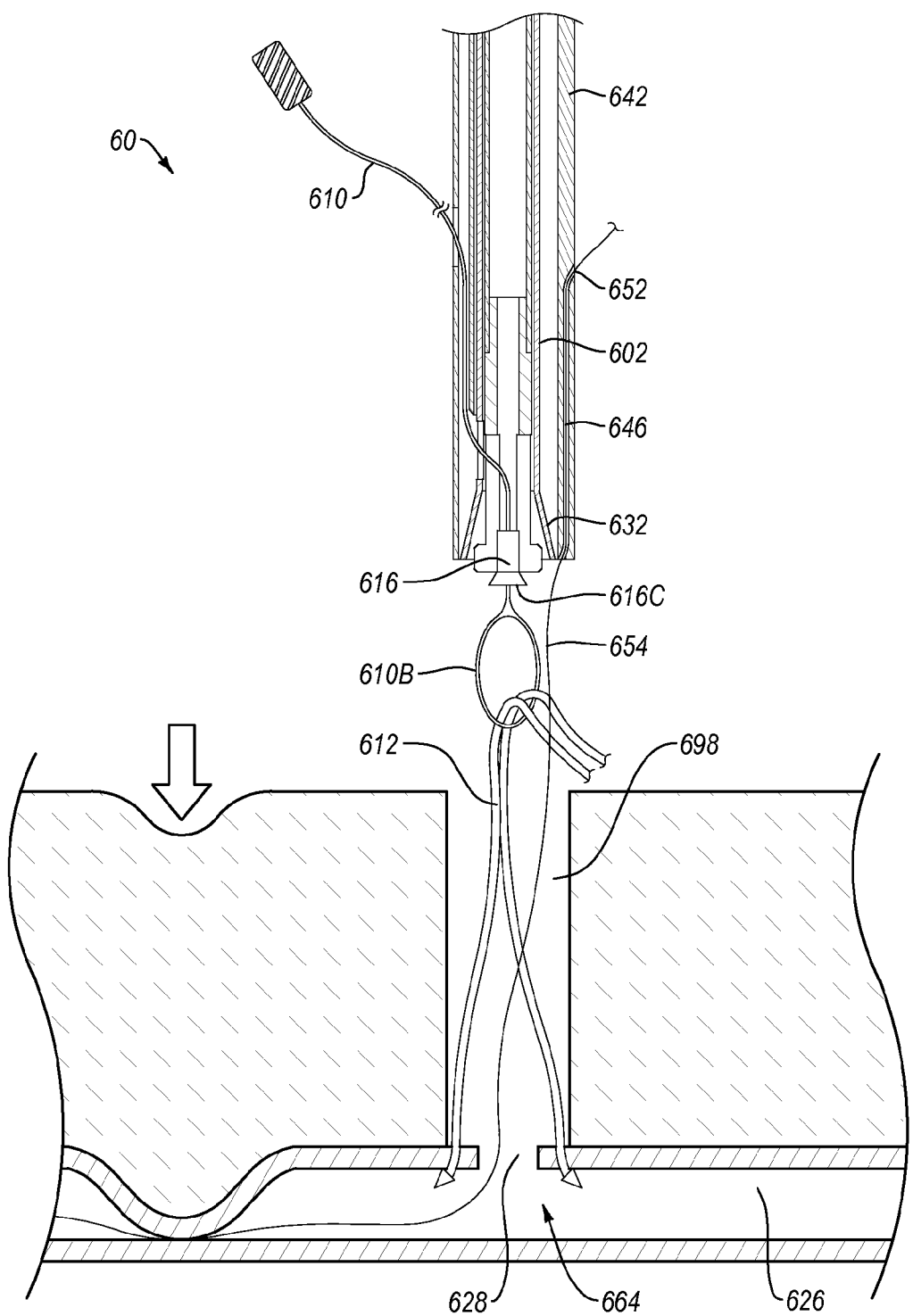
FIG. 7A is a partial cross sectional view illustrating an exemplary step in a method of securing suture lengths over a vessel repair site with the suture securing system shown in FIG. 6B.

Referring now to FIG. 7A, once the suture lengths 612 have been delivered through a vessel wall 626 on opposing sides of the puncture 628 and a procedural guide wire has been inserted into the puncture 628, the method can begin by positioning the distal portion of the barrel 602 in proximity with a tissue tract 698 at the vessel repair site 664 while the snare 610 is extended through the system 60 and the knot replacement element 616. The snare 610 may be sized, shaped and configured to move freely through the system 60, including through an inner lumen 616C of the knot replacement element 616.

With the distal portion of the barrel 602 in proximity with the tissue tract 698 and the snare 610 extended through the system 60 and through the knot replacement element 616, manual pressure may be applied to the vessel wall 626 for temporary hemostasis. The procedural guide wire 654 can then be fed proximally through the side lumen 646 of the sheath 642 and the suture lengths 612 can be fed through the snare portion 610B of the snare 610. The suture lengths 612 can then be secured to the snare 610 by twisting the snare portion 610B about the suture lengths 612, tying the suture lengths 612 onto the snare portion 610B, or any other means suitable to secure the suture lengths 612 to the snare 610.

Figure 7B:
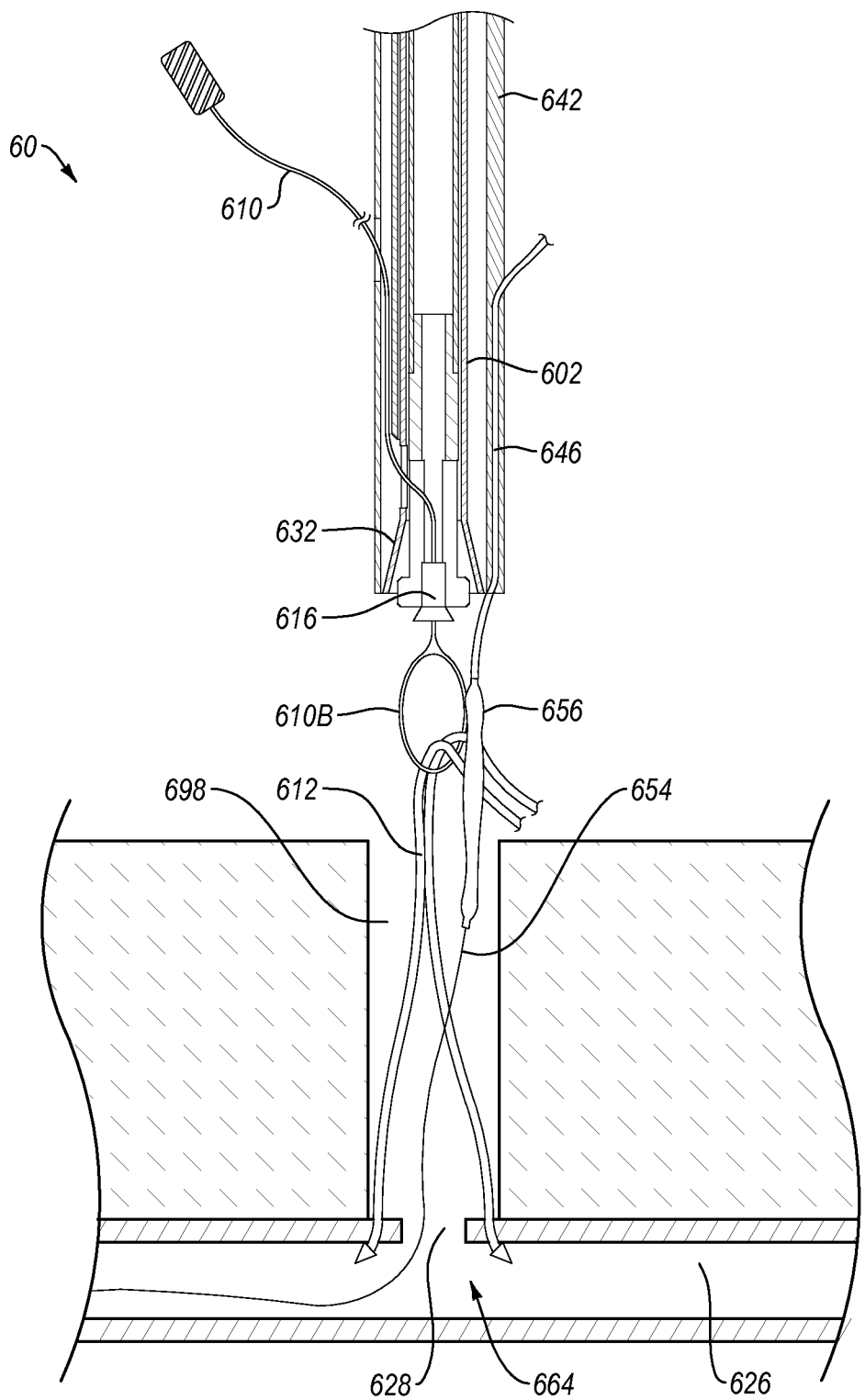
FIG. 7B is a partial cross sectional view illustrating an exemplary step in a method of securing suture lengths over a vessel repair site with the suture securing system shown in FIG. 6B.
Figure 7C:
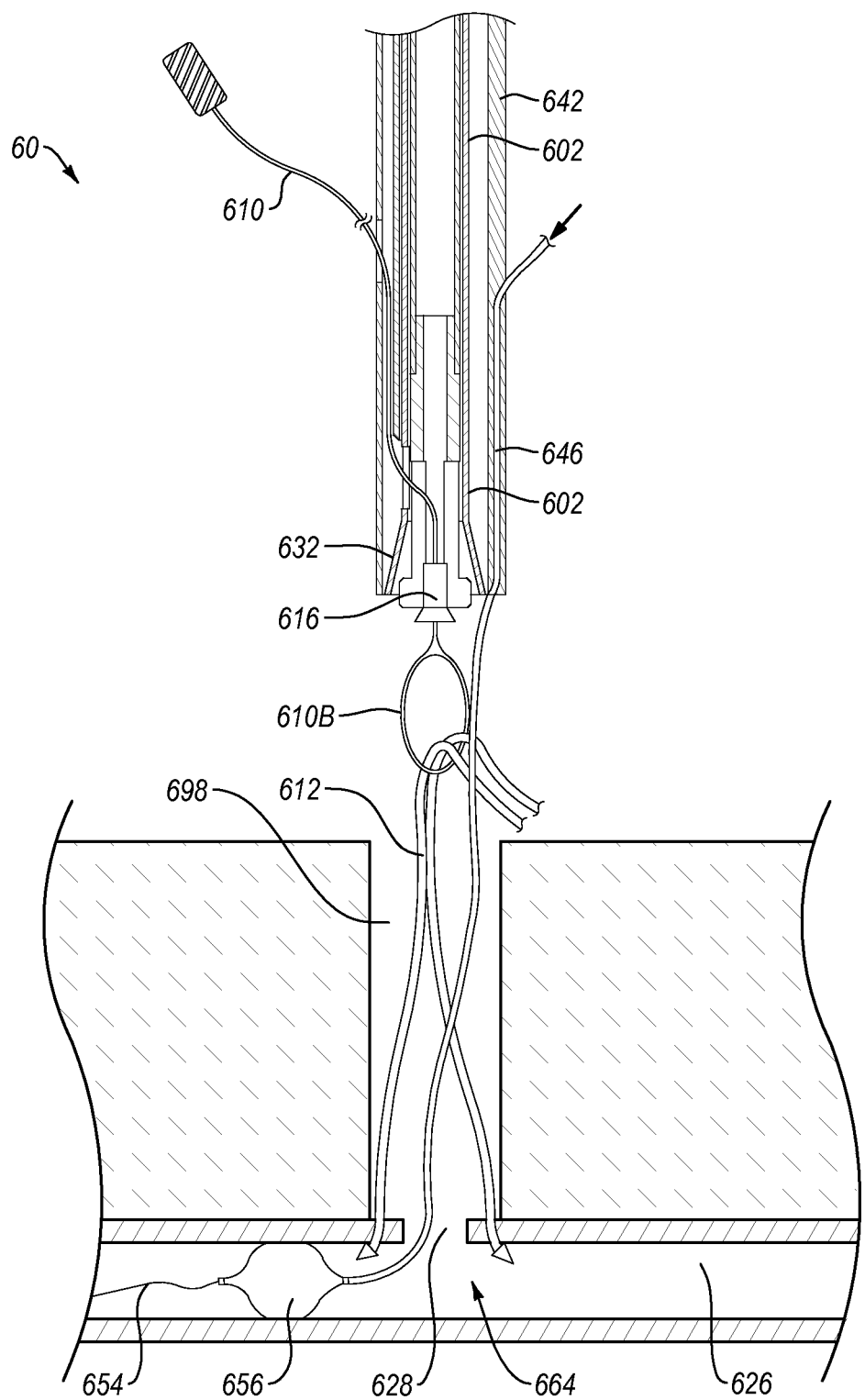
FIG. 7C is a partial cross sectional view illustrating an exemplary step in a method of securing suture lengths over a vessel repair site with the suture securing system shown in FIG. 6B.

Referring now to FIGS. 7B and 7C, a balloon catheter 656 may be advanced over the procedural guide wire 654 and through the side lumen 646 of the sheath 642 to position the balloon catheter 656 within the puncture 628. In another embodiment, the balloon catheter 656 may be advanced over the procedural guide wire 654 before the procedural guide wire 654 is fed through the side lumen 646 of the sheath 642. With the balloon catheter 656 in place, the balloon catheter 656 may be inflated for temporary hemostasis and the manual pressure may be released from the vessel wall 626.

Figure 7D:
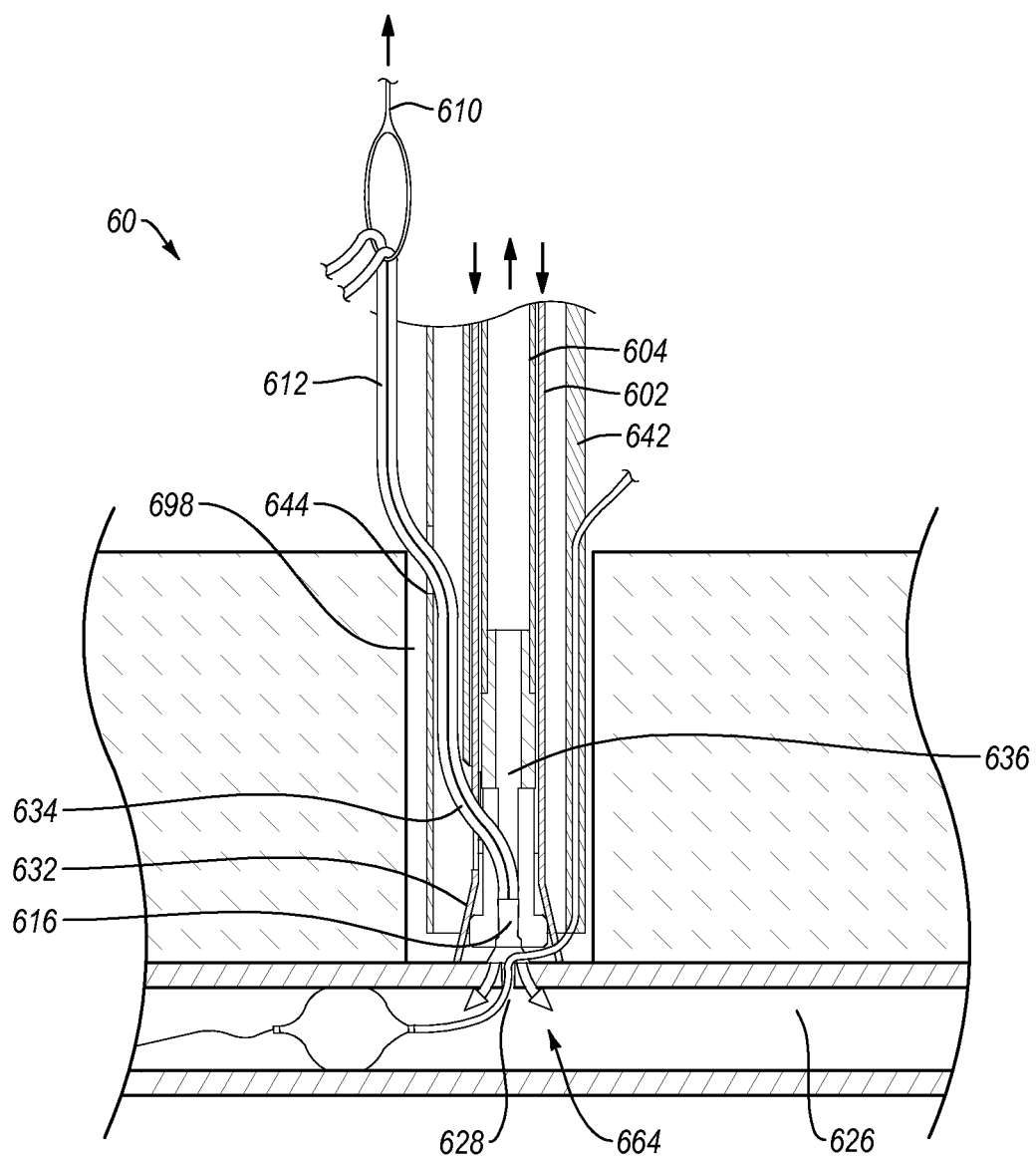
FIG. 7D is a partial cross sectional view illustrating an exemplary step in a method of securing suture lengths over a repair site in body tissue with the suture securing system shown in FIG. 6B.

Referring now to FIG. 7D, the snare 610, along with the suture lengths 612, can then be drawn proximally through the knot replacement element 616, into the barrel 602, through the side port 634 of the barrel 602, and out the side port 644 of the sheath 642. Once the suture lengths 612 have been pulled out of the side port 644, the flared portion 632 of the barrel 602 and the knot replacement element 616 may be advanced toward an outer surface of the vessel wall 626. Advancing the barrel 602 to the vessel wall 626 passes the knot replacement element 616 over the suture lengths 612. The suture lengths 612 may then be tensioned to pull the puncture 628 substantially closed, as shown. The suture lengths 612 may be tensioned with the snare 610, manually, or by any other suitable means.

Still referring to FIG. 7D, once the knot replacement element 616 reaches the outer surface of the vessel wall 626 and the puncture 628 is substantially closed by the tensioned suture lengths 612, the cam lever 630 (not shown) may be rotated to cause the collet 636 to crimp the knot replacement element 616 onto the suture lengths 612.

Figure 7E:
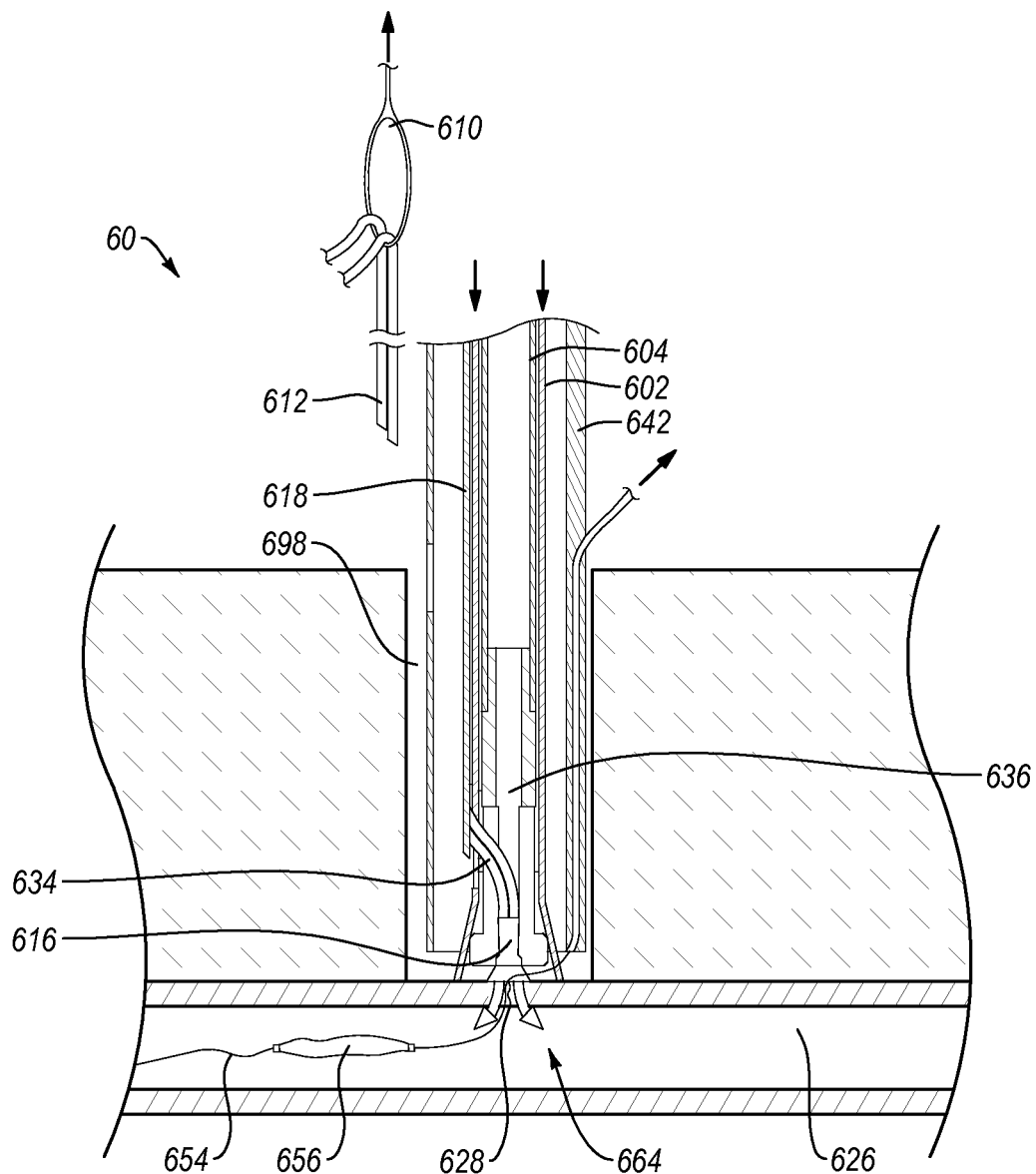
FIG. 7E is a partial cross sectional view illustrating an exemplary step in a method of securing suture lengths over a repair site in body tissue with the suture securing system shown in FIG. 6B.

As shown in FIG. 7E, after hemostasis is confirmed, the balloon catheter 656 can be deflated and removed through the substantially closed puncture 628. The procedural guide wire 654 may also be removed through the substantially closed puncture 628. A user may then apply minor tension to the suture lengths 612 and minor compression to the knot replacement element 616 with the collet 636 to close off any hole left by the balloon catheter 656 and the procedural guide wire 654. The trimmer member 618 may then be advanced into the extended position to trim the suture lengths 612 extending from the side port 634 of the barrel 602. Such a configuration of the system 60 allows the suture lengths 612 to be trimmed relatively close to the closed puncture 628 thereby reducing the risk of infection.

Figure 7F:
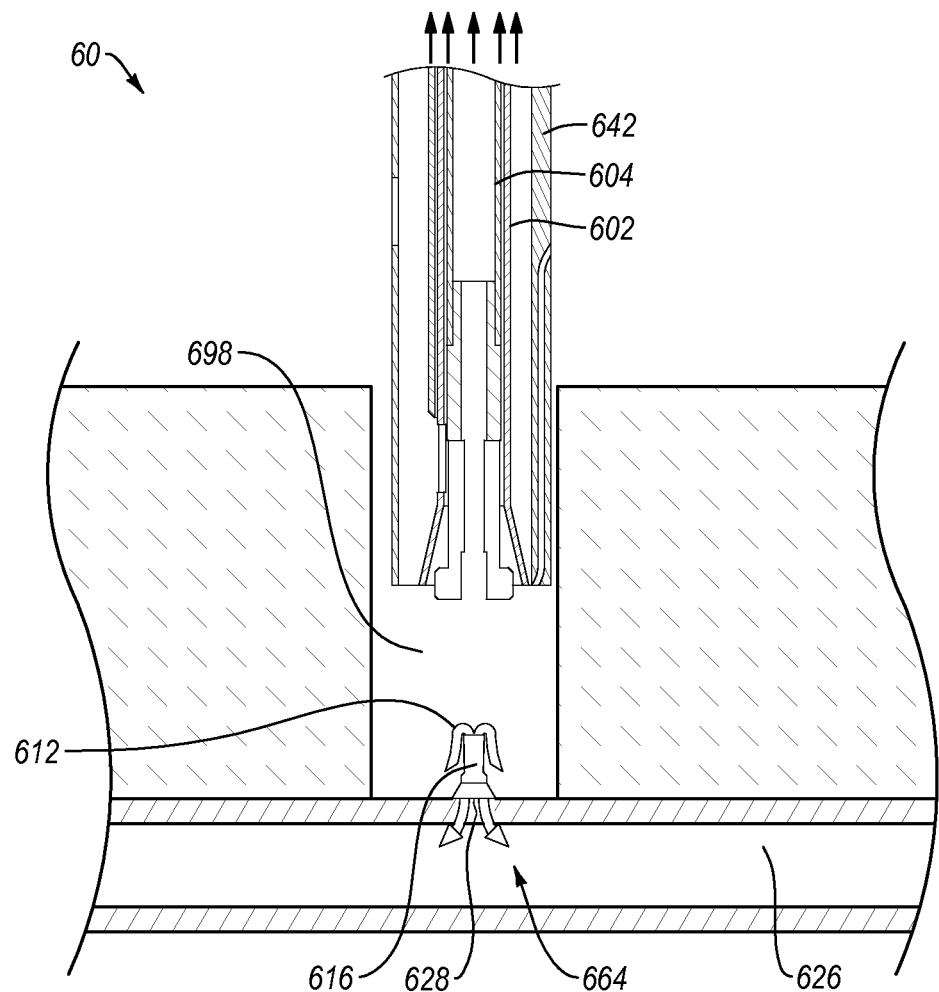
FIG. 7F is a partial cross sectional view illustrating an exemplary step in a method of securing suture lengths over a repair site in body tissue with the suture securing system shown in FIG. 6B.

As shown in FIG. 7F, the system 60 can then be removed from the tissue tract 698, leaving the knot replacement element 616 fastened to the tensioned suture lengths 612 over the closed puncture 628. Accordingly, as shown in FIGS. 7A-7F, the system 60 can be configured to tension and secure suture lengths over a vessel repair site without tying a knot in the suture lengths.

Figure 8A:
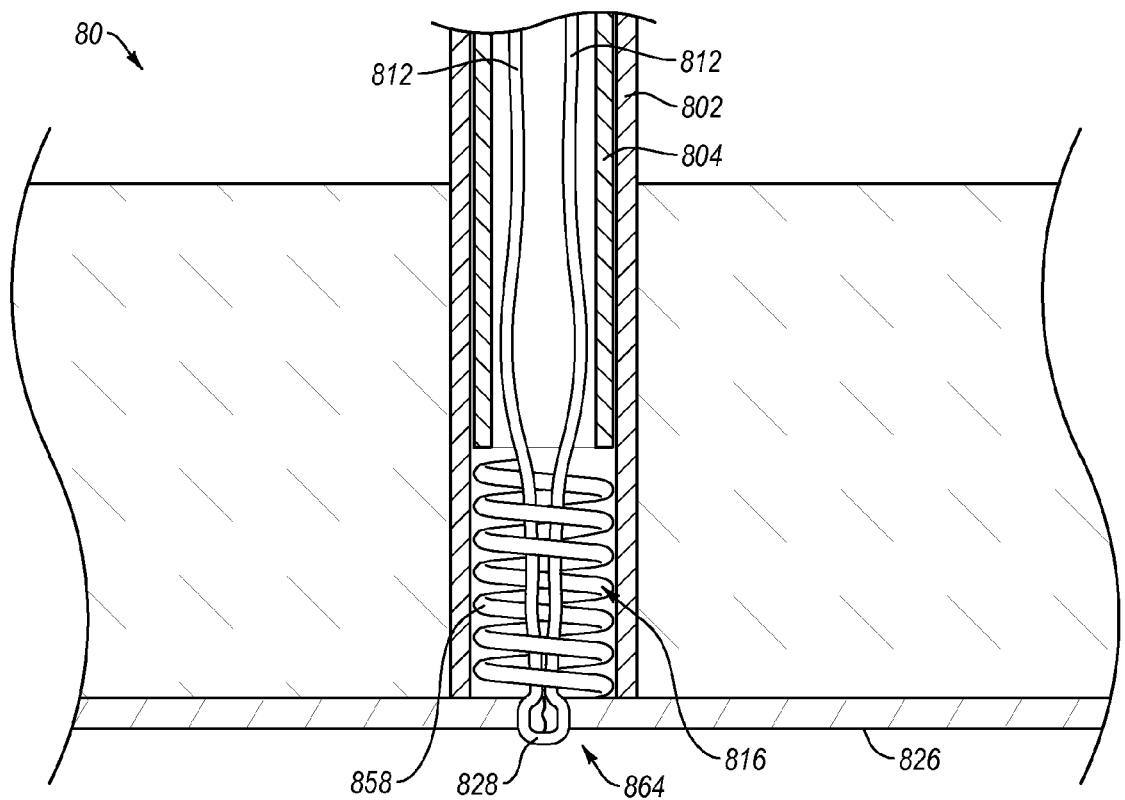
FIG. 8A is a partial cross sectional view illustrating a knot replacement element in a first position over a vessel repair site according to one example.
Figure 8B:
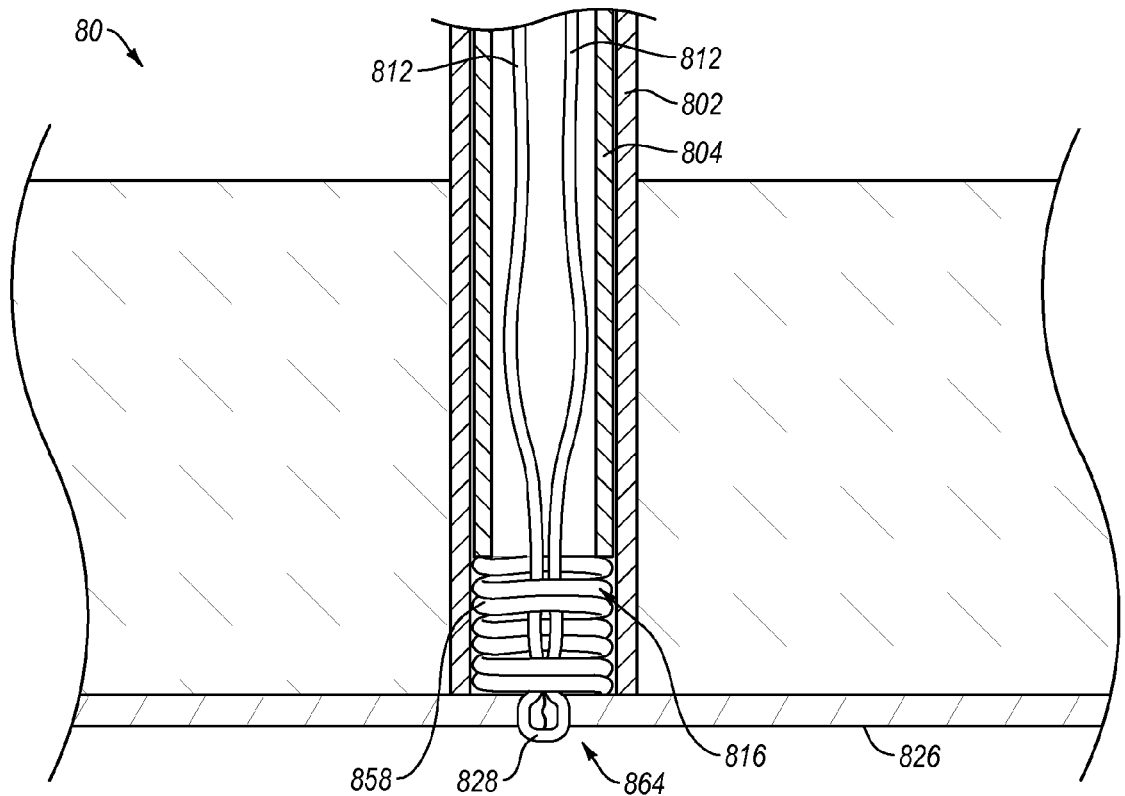
FIG. 8B is a partial cross sectional view illustrating the knot replacement element shown in FIG. 8A in a second position over the vessel repair site according to one example.

FIGS. 8A through 8D illustrate another embodiment of a knot replacement element 816. The knot replacement element 816 may be a coil spring having a plurality of coils 858 made from standard metal, bioabsorbable metal or plastic, or any other suitable material. While the coils 858 are illustrated having a circular cross-sectional shape, the coils 858 may have a triangular, square, rectangular, oval, or any other shape suitable to create coiled ring. As shown in FIG. 8A, the coils 858 of the coil spring may form rings or loops having uniform diameters. A snare (not shown) and/or suture lengths 812 may be looped in and out of the coils 858 in any suitable pattern to draw the suture lengths 812 through the knot replacement element 816. For example, the suture lengths 812 may be looped inside of two of the coils 858, outside of two of the coils 858, and then inside of two of the coils 858. In another embodiment, the suture lengths 812 may be looped outside of two of the coils 858, inside of two of the coils 858, and then outside of two of the coils 858. In other embodiments, the suture lengths 812 may be looped inside and outside of the coils 858 in an alternating fashion. The knot replacement element 816 may be moveable from a first position (shown in FIG. 8A) wherein suture lengths 812 may move in and out of the coils 858 to a second position (shown in FIG. 8B) wherein the coils 858 are compressed or crunched together to create stop or pinch points to hold the suture lengths 812. As shown in FIG. 8A, the coils 858 may be separated by gaps sized and configured to allow the suture lengths 812 to freely move between the coils 858. However, once the knot replacement element 816 is moved into the second position, the knot replacement element 816 may be configured to remain in the second position. In other embodiments, the coils 858 may include barbs, teeth, hooks or other friction elements configured to grab or snag the suture lengths 812 when the knot replacement element 816 is in the second position. Such a configuration can assist the knot replacement element 816 in securing the suture lengths 812 over a vessel repair site 864 in a vessel wall 826, without tying a knot in the suture lengths 812. As shown in FIGS. 8A and 8B, the knot replacement element 816 may be loaded onto a suture securing system 80 which may be similar in many respects to the systems 10, 40 and 60. Either before or after loading the knot replacement element 816 on the suture securing system 80, the suture lengths 812 may be drawn through the knot replacement element 816. The suture lengths 812 may then be drawn through the suture securing system 80. The suture securing system 80 and the knot replacement element 816 may then be advanced approximate a puncture 828 in the vessel wall 826. The suture lengths 812 may then be tensioned to close the puncture 828.

As shown in FIG. 8B, the suture securing system 80 may then move the coils 858 of the knot replacement element 816 into the second position. Specifically, a shaft 804 may be advanced within a barrel 802 to compress the knot replacement element 816. With the coils 858 of the knot replacement element 816 in the second position, the suture lengths 812 can be considered secured because the suture lengths 812 are tensioned and movement of the suture lengths 812 through the vessel wall 826 is restricted in both the proximal and distal directions by the knot replacement element 816.

Figure 8C:
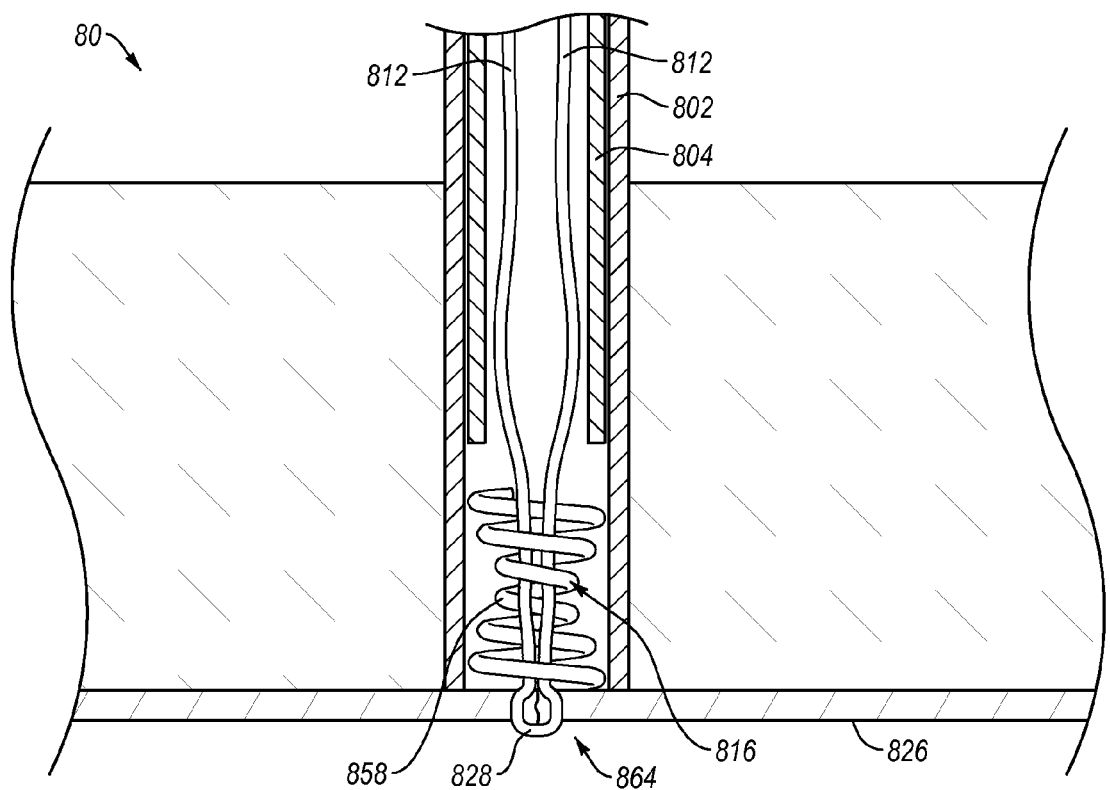
FIG. 8C is a partial cross sectional view illustrating a knot replacement element in a first position over a vessel repair site according to one example.
Figure 8D:
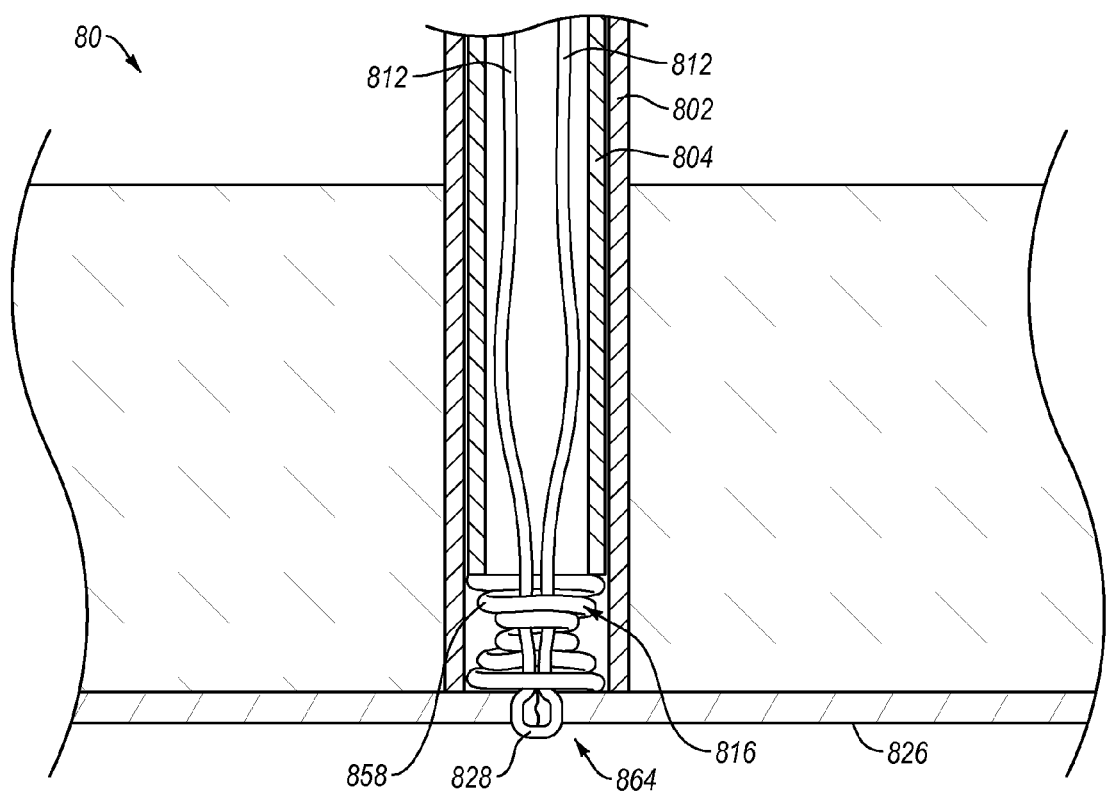
FIG. 8D is a partial cross sectional view illustrating the knot replacement element shown in FIG. 8C in a second position over the vessel repair site according to one example.

As shown in FIGS. 8C and 8D, in other embodiments, the coils 858 may form loops or rings have varying diameters such that the knot replacement 816 has an hour-glass shape or any other shape suitable to function as a knot in the suture lengths 812 such as an oval shape or a cone shape. A non-uniform configuration may facilitate looping the snare (not shown) and/or suture lengths 812 through the coils 858. In addition, the knot replacement element 816 having varying diameter coils 858 may also create multiple layers of pinch points in the second position as the coils 858 are compressed together at varying distances from a longitudinal axis of the knot replacement element 816. Such a configuration may improve the ability of the knot replacement element 816 to hold the suture lengths 812 over a closed puncture 828 by reinforcing type strength to the knot replacement element 816.

Figure 9A:
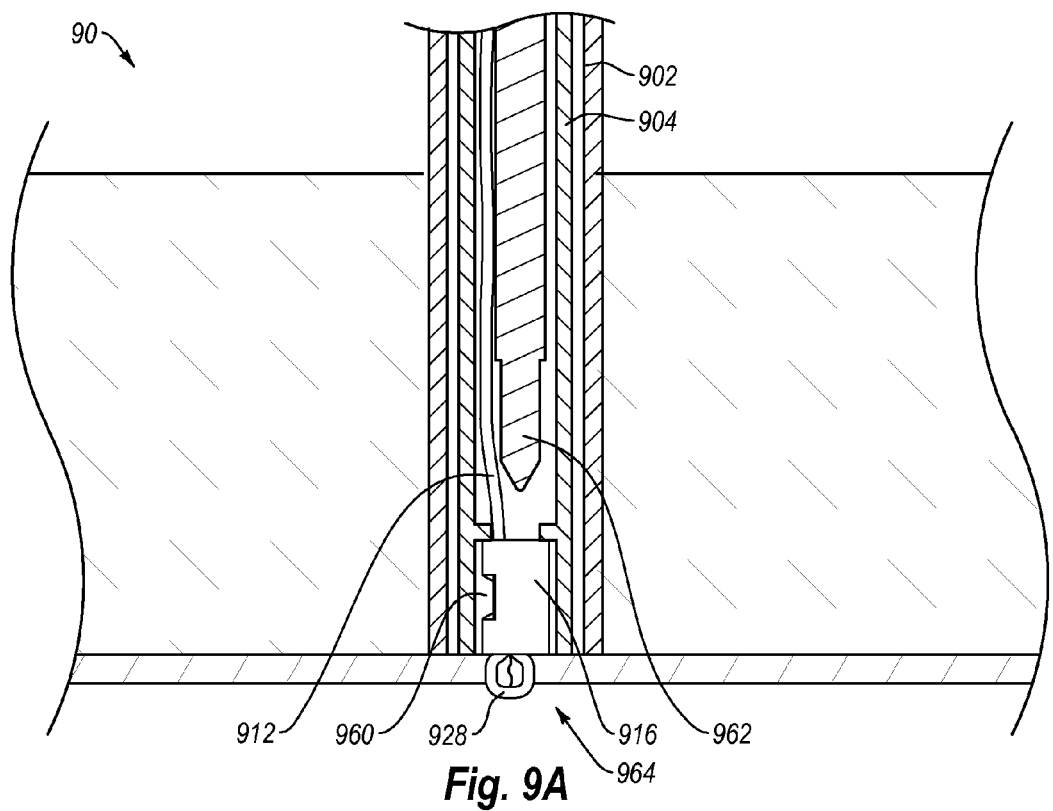
FIG. 9A is a partial cross sectional view illustrating a knot replacement element over a vessel repair site according to one example.
Figure 9B:
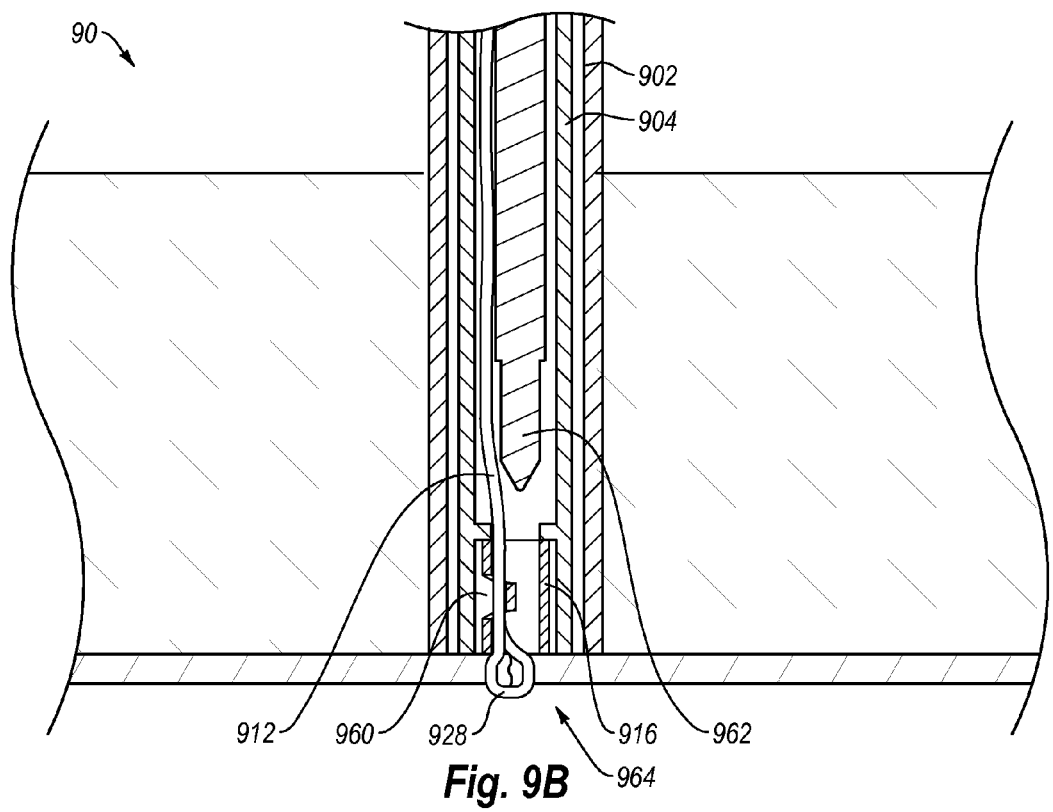
FIG. 9B is a partial cross sectional view illustrating a cross sectional view of the knot replacement element shown in FIG. 9A over the vessel repair site.
Figure 9C:
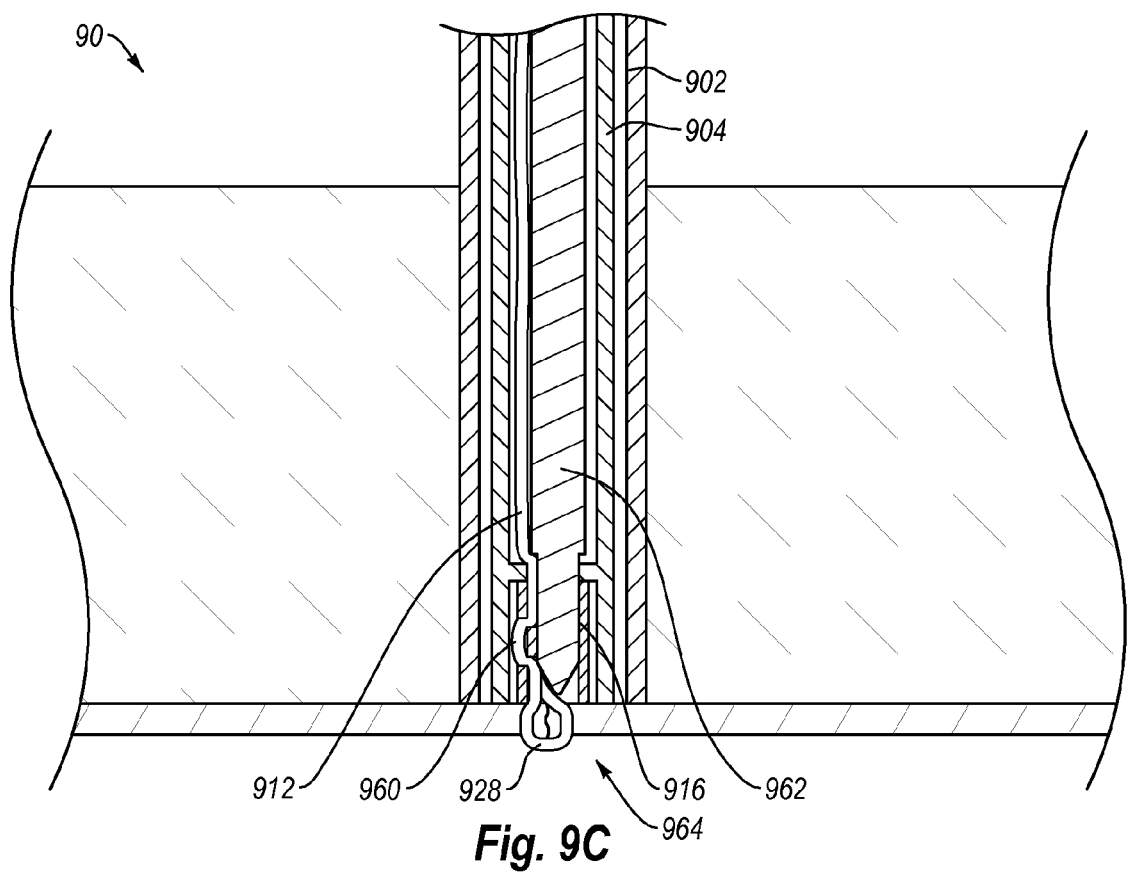
FIG. 9C is a partial cross sectional view illustrating the knot replacement element shown in FIG. 9B secured on suture lengths over the vessel repair site.

FIGS. 9A through 9C illustrate another embodiment of a knot replacement element 916. The knot replacement element 916 may comprise a tube made from standard metal, bioabsorbable metal or plastic, or any other material suitable to function as a knot on suture lengths 912 over a vessel repair site 964. The knot replacement element 916 may include an indentation 960 formed in a sidewall of the knot replacement element 916. The indentation 960 may have an upper edge and a lower edge separated from the side wall of the knot replacement element 916 such that the suture lengths 912 may be drawn through the indentation 960 manually or by a snare (not shown). FIG. 9B illustrates a cross sectional view of the knot replacement element 916 as shown in FIG. 9A. As shown, a user may feed the suture lengths 912 inside of the sidewall of the knot replacement element 916, outside a back wall of the indentation 960, and then inside of the sidewall of the knot replacement element 916. While a single indentation 960 is shown, the knot replacement element 916 may include any number of indentations. For example, knot replacement element 916 may include two indentations, one above the other in the sidewall of the knot replacement element 916. The knot replacement element 916 may be loaded onto a suture securing device 90 which may be similar in many respects to systems 10, 40, 60, and 80. As shown, the suture securing system 90 may include a mandrel 962 disposed on a distal end of an inner shaft 904 that is moveable within a barrel 902.

As shown in FIG. 9C, the mandrel 962 may be sized, shaped and configured to selectively fit within the knot replacement element 916. Specifically, the mandrel 962 may be configured to push the indentation 960 outward as the mandrel is advanced through the knot replacement element 916 by the shaft 904. The suture lengths 912 looping in and out the knot replacement element 912 and the indentation 960 may be held in pinch points created between the back wall of the indentation 960 and the side wall of the knot replacement element 916. As with other embodiments of the knot replacement elements, such a configuration can allow the knot replacement element 916 to fasten the suture lengths 912 together over a vessel repair site, without tying a knot in the suture lengths 912.

Figure 10A:
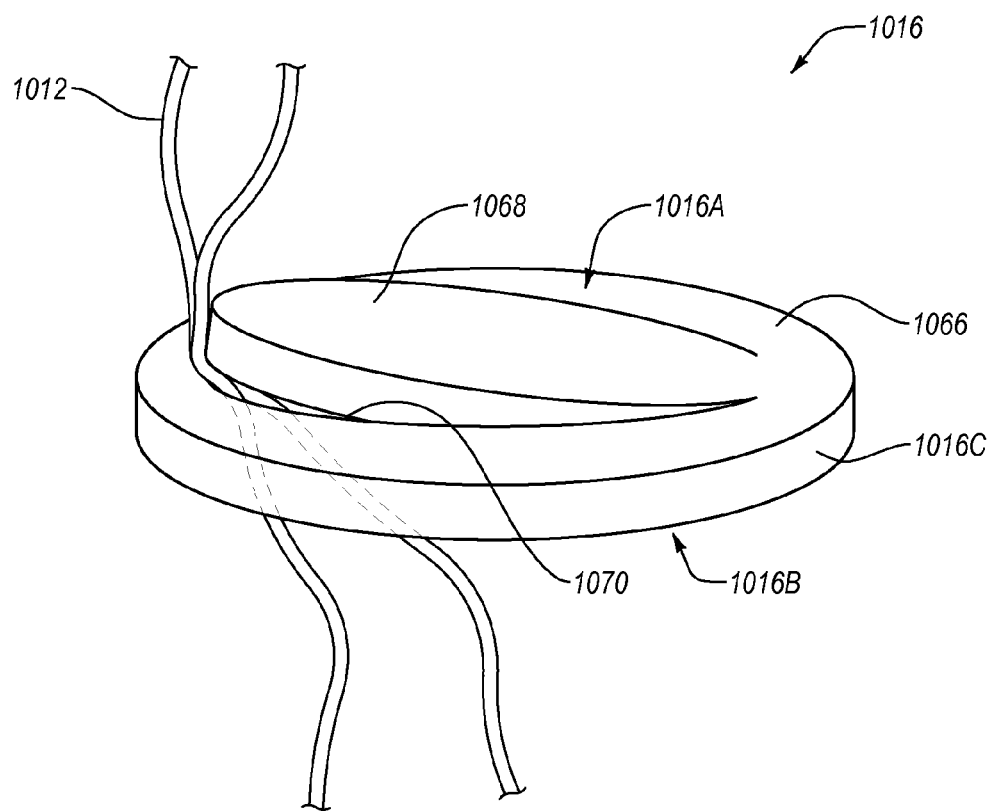
FIG. 10A is a side perspective view illustrating a knot replacement element with suture lengths extending therethrough according to one example.
Figure 10B:
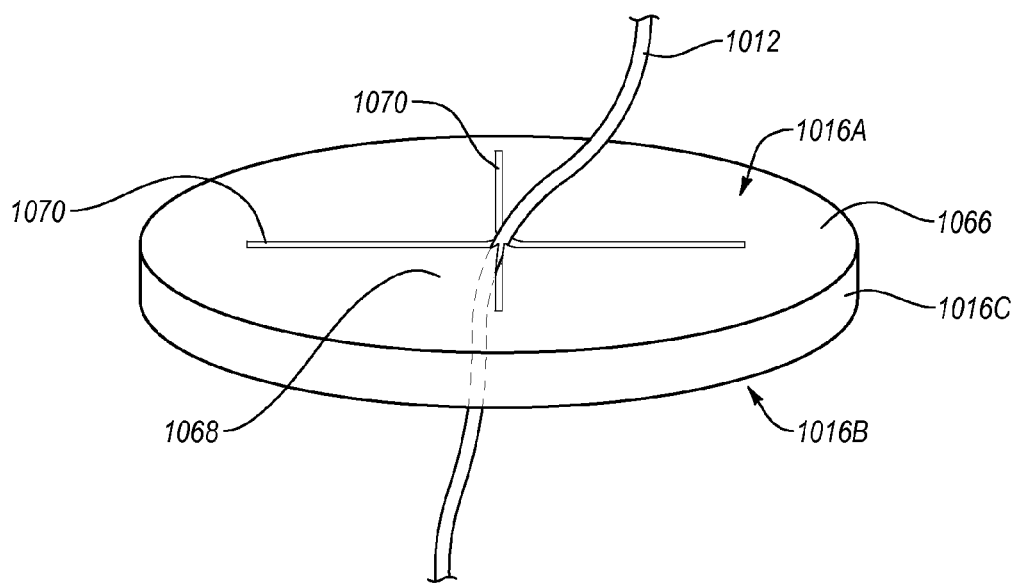
FIG. 10B is a side perspective view illustrating a knot replacement element according to one example.

FIGS. 10A through 10D illustrate yet another embodiment of a knot replacement element 1016. The knot replacement element 1016 may comprise a disc made from metal, bioabsorbable metal or plastic, or any other material suitable to function as a knot on suture lengths 1012 over a vessel repair site 1064. The knot replacement element 1016 may include an upper surface 1016A, a lower surface 1016B, a side surface 1016C, an outer base region 1066 and an inner locking region 1068. The inner locking region 1068 may be defined at least partially by one or more slits 1070 extending between the upper surface 1016A and the lower surface 1016B and have at least one portion connected to the outer base region 1066. As shown in FIG. 10A, the one or more slits 1070 may include a single slit circumferentially extending around an interior portion of the knot replacement element 1016. In other embodiments, the one or more slits 1070 include a pair of slits in a cross or x-shaped configuration as shown in FIG. 10B. In other embodiments, the one or more slits may have an s-shaped configuration, a u-shaped configuration, an isosceles trapezium configuration, a triangular configuration, or any other configuration suitable to create the inner locking region 1068.

The knot replacement element 1016 may be moveable between a first position, wherein the outer base region 1066 and the inner locking region 1068 are biased to lie in a generally common plane, and a second position, wherein at least a portion of the inner locking region 1068 extends above the upper surface 1016A on the outer base region 1066 to form a temporary opening in the knot replacement element 1016 configured to receive suture lengths 1012.

In one embodiment, the knot replacement element 1016 may have elastic properties and be biased toward the first position. When the knot replacement element 1016 is compressed, the knot replacement element can move to the second position and when the compression is released the knot replacement element can return to the first position. Thus, pressure can be exerted on the side surface 1016C of the knot replacement element 1016 to move the knot replacement element 1016 into the second position so that the suture lengths 1012 can be passed through the temporary opening. When the pressure is released, the knot replacement element 1016 can be self-biased to move to the first position to close the temporary opening and lock the suture lengths 1012 between the outer base region 1066 and the inner locking region 1068. In other embodiments, the knot replacement element 1016 may be made from one or more materials having shape memory properties such that the knot replacement element 1016 can move between the first position and the second position in response to triggers such as predetermined temperatures or pressures as discussed in more detail below. Moreover, the knot replacement element 1016 may include features to prevent to knot replacement element 1016 from unexpectedly moving away from the first position and/or to prevent the inner locking region 1068 from "popping" beyond the lower surface 1016B of the knot replacement element 1016. For example, the knot replacement element 1016 can be made with predetermined tolerances such that the presence of the suture lengths 1012 within the one or more slits 1070 can lock the outer base region 1066 and the inner locking region 1068 together in the first position. In addition, the one or more slits 1070 can include a tapered profile to prevent a "pop" through, a heat set can be used to crimp the outer base region 1066 to the inner locking region 1068 once the suture lengths 1012 have been secured, or other means suitable to prevent the knot replacement element 1016 from unexpectedly moving away from the first configuration and/or to prevent the inner locking region 1068 from "popping" beyond the lower surface 1016B of the knot replacement element 1016 is possible.

In other embodiments, the one or more slits 1070 may include barbs, teeth, hooks or other friction elements configured to grab or snag the suture lengths 1012 when the knot replacement element 1016 is in the first configuration. Such a configuration can assist the knot replacement element 1016 in securing the suture lengths 1012 over a vessel repair site 1064 (shown in FIGS. 10C and 10D) in a vessel wall 1026 (shown in FIGS. 10C and 10D), without tying a knot in the suture lengths 1012.

Figure 10C:
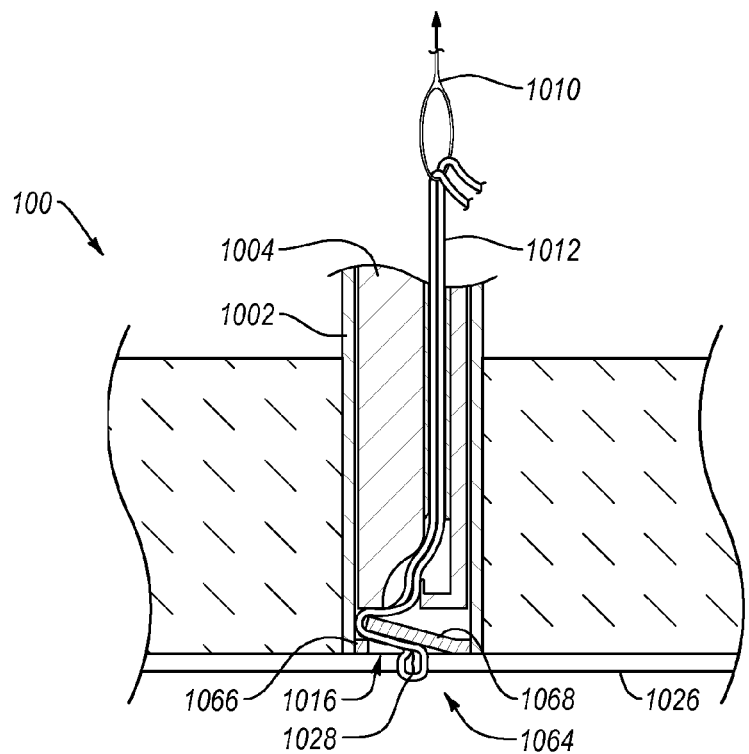
FIG. 10C is a partial cross sectional view illustrating the knot replacement element shown in FIG. 10A over the vessel repair site.
Figure 10D:
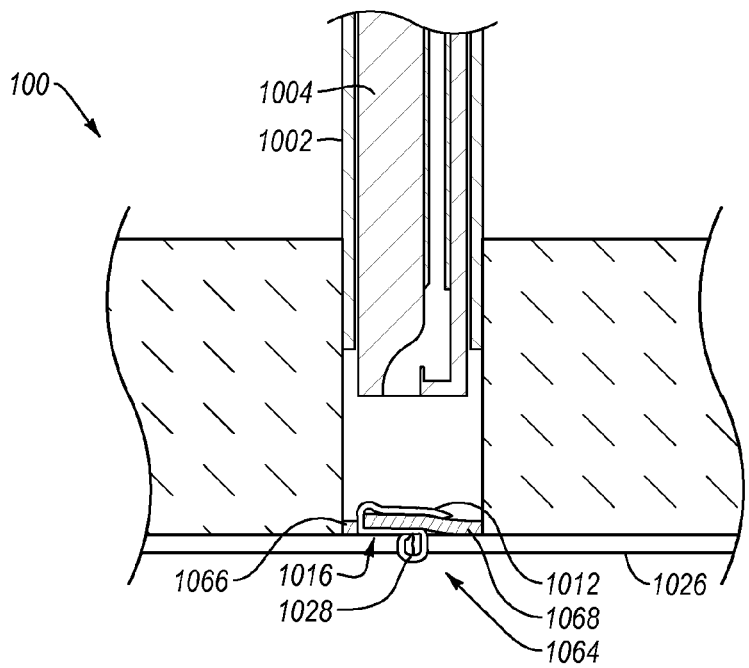
FIG. 10D is a partial cross sectional view illustrating the knot replacement element shown in FIG. 10C secured on suture lengths over the vessel repair site.

FIGS. 10C and 10D are partial cross sectional views illustrating the knot replacement element 1016 shown in FIG. 10A over the vessel repair site 1064. As shown in FIGS. 10C and 10D, the knot replacement element 1016 may be loaded onto a suture securing system 100 which may be similar in many respects to the systems 10, 40, 60, 80, and 90. The knot replacement element 1016 and/or a barrel 1002 of the suture securing system 100 may be sized and configured such that loading the knot replacement element 1016 into the barrel 1002 compresses the knot replacement element 1016 to move the knot replacement element 1016 toward the second position. With the knot replacement element 1016 in the second position, the suture lengths 1012 may be drawn through the temporary opening formed in the knot replacement element 1016 and through the suture securing system 100 by a snare 1010 or other suitable means. The suture securing system 100 and the knot replacement element 1016 may be advanced approximate a puncture 1028 in the vessel wall 1026 as shown in FIG. 10C. The suture lengths 1012 may then be tensioned to close the puncture 1028.

As shown in FIG. 10D, a shaft 1004 may be advanced within the barrel 1002 to eject the knot replacement element 1016 from the suture securing system 100 thereby releasing pressure exerted by the barrel 1002 on the knot replacement element 1016 and moving the knot replacement element 1016 toward the first position to lock onto the suture lengths 1012. As shown, in the first position the inner locking region 1068 of knot replacement element 1016 may be self-biased toward a common plane with the outer base region 1066 to lock the suture lengths 1012 between the inner locking region 1068 and the outer base region 1066 of the knot replacement element 1016. With the knot replacement element 1016 locked onto the suture lengths 1012 in the first position, the suture lengths 1012 can be considered secured because the suture lengths 1012 are tensioned and movement of the suture lengths 1012 through the vessel wall 1026 is restricted in both the proximal and distal directions by the knot replacement element 1016. The suture lengths 1012 may then be trimmed and the suture securing system 100 may be removed from the vessel repair site 1064. Optionally, the suture lengths 1012 may be trimmed simultaneously or nearly simultaneously with the barrel 1002 ejecting the knot replacement element 1016 from the suture securing system 100.

Embodiments of the knot replacement element, snare and the like may include a material made from any of a variety of known suitable biocompatible materials, such as a biocompatible shape memory material (SMM). For example, the SMM may be shaped in a manner that allows for a delivery orientation of the knot replacement element while within the suture securing system, but may automatically retain the memory shape of the knot replacement element once ejected from the system to secure the suture lengths. SMMs have a shape memory effect in which they may be made to remember a particular shape. Once a shape has been remembered, the SMM may be bent out of shape or deformed and then returned to its original shape by unloading from strain or heating. Typically, SMMs may be shape memory alloys (SMA) comprised of metal alloys, or shape memory plastics (SMP) comprised of polymers. The materials may also be referred to as being superelastic.

Usually, an SMA may have an initial shape that may then be configured into a memory shape by heating the SMA and conforming the SMA into the desired memory shape. After the SMA is cooled, the desired memory shape may be retained. This allows for the SMA to be bent, straightened, twisted, compacted, and placed into various contortions by the application of requisite forces; however, after the forces are released, the SMA may be capable of returning to the memory shape. The main types of SMAs are as follows: copper-zinc-aluminum; copper-aluminum-nickel; nickel-titanium (NiTi) alloys known as nitinol; nickel-titanium platinum; nickel-titanium palladium; and cobalt-chromium-nickel alloys or cobalt-chromium-nickel-molybdenum alloys known as elgiloy alloys. The temperatures at which the SMA changes its crystallographic structure are characteristic of the alloy, and may be tuned by varying the elemental ratios or by the conditions of manufacture.

For example, the primary material of snare and/or the knot replacement element may be of a NiTi alloy that forms superelastic nitinol. Also, additional materials may be added to the nitinol depending on the desired characteristic. The alloy may be utilized having linear elastic properties or non-linear elastic properties.

An SMP is a shape-shifting plastic that may be fashioned into the snare and/or knot replacement element in accordance with the present disclosure. Also, it may be beneficial to include at least one layer of an SMA and at least one layer of an SMP to form a multilayered body; however, any appropriate combination of materials may be used to form a multilayered device. When an SMP encounters a temperature above the lowest melting point of the individual polymers, the blend makes a transition to a rubbery state. The elastic modulus may change more than two orders of magnitude across the transition temperature (Ttr). As such, an SMP may be formed into a desired shape of an endoprosthesis by heating it above the Ttr, fixing the SMP into the new shape, and cooling the material below Ttr. The SMP may then be arranged into a temporary shape by force and then resume the memory shape once the force has been released. Examples of SMPs include, but are not limited to, biodegradable polymers, such as oligo (ε-caprolactone)diol, oligo(ρ-dioxanone)diol, and non-biodegradable polymers such as, polynorborene, polyisoprene, styrene butadiene, polyurethane-based materials, vinyl acetate-polyester-based compounds, and others yet to be determined. As such, any SMP may be used in accordance with the present disclosure.

The snare, the knot replacement element, and the like may have at least one layer made of an SMM or suitable superelastic material and other suitable layers may be compressed or restrained within the system, and then deployed over a vessel repair site so that it transforms to the trained shape. For example, the knot replacement element and snare can transition to secure onto the suture lengths.

Also, the snare, the knot replacement element, or other aspects or components of the system may be comprised of a variety of known suitable deformable materials, including stainless steel, silver, platinum, tantalum, palladium, nickel, titanium, nitinol, nitinol having tertiary materials (U.S. 2005/0038500, which is incorporated herein by reference, in its entirety), niobium-tantalum alloy optionally doped with a tertiary material (U.S. 2004/0158309, 2007/0276488, and 2008/0312740, which are each incorporated herein by reference, in their entireties) cobalt-chromium alloys, or other known biocompatible materials. Such biocompatible materials may include a suitable biocompatible polymer in addition to or in place of a suitable metal. The polymeric knot replacement element may include biodegradable or bioabsorbable materials, which may be either plastically deformable or capable of being set over a vessel repair site.

In one embodiment, the snare and/or knot replacement element may be made from a superelastic alloy such as nickel-titanium or nitinol, and includes a ternary element selected from the group of chemical elements consisting of iridium, platinum, gold, rhenium, tungsten, palladium, rhodium, tantalum, silver, ruthenium, or hafnium. The added ternary element improves the radiopacity of the nitinol knot replacement element. The nitinol knot replacement element has improved radiopacity yet retains its superelastic and shape memory behavior and further maintains a thin body thickness for high flexibility.

In one embodiment, the snare and/or the knot replacement element may be made at least in part of a high strength, low modulus metal alloy comprising Niobium, Tantalum, and at least one element selected from the group consisting of Zirconium, Tungsten, and Molybdenum.

In further embodiments, the snare and/or the knot replacement element may be made from or be coated with a biocompatible polymer. Examples of such biocompatible polymeric materials may include hydrophilic polymer, hydrophobic polymer biodegradable polymers, bioabsorbable polymers, and monomers thereof. Examples of such polymers may include nylons, poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, polyanhydrides, polyanhydride-co-imides, polyesters, polyorthoesters, polycaprolactones, polyesters, polyanydrides, polyphosphazenes, polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyrosines, poly (beta-hydroxybutyrate), polyhydroxybutyrate-hydroxyvaleric acids, polyethylenes, polypropylenes, polyaliphatics, polyvinylalcohols, polyvinylacetates, hydrophobic/hydrophilic copolymers, alkylvinylalcohol copolymers, ethylenevinylalcohol copolymers (EVAL), propylenevinylalcohol copolymers, polyvinylpyrrolidone (PVP), combinations thereof, polymers having monomers thereof, or the like.

The coatings can also be provided on the system or components thereof to facilitate the loading or delivery of beneficial agents or drugs, such as therapeutic agents, pharmaceuticals and radiation therapies.

The invention is susceptible to various modifications and alternative means, and specific examples thereof have been shown by way of example in the drawings and are herein described in detail. It should be understood, however, that the invention is not to be limited to the particular systems or methods disclosed, but to the contrary; the invention is to cover all modifications, equivalents, and alternatives falling within the spirit and scope of the claims.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A suture securing system for use in closing a vessel puncture site while eliminating the need for suture lengths to be manually tied in knots, the system comprising:
    an elongate body comprising a shaft and a barrel, the shaft having a proximal end and a distal portion, the barrel having a proximal end and a distal end comprising an opening, the barrel being mounted on the shaft such that the shaft can slide relative to the barrel, the elongate body being configured for insertion through a tissue tract to position the distal end of the barrel adjacent the vessel puncture site;
    a knot replacement element having an outer surface and an inner lumen extending therethrough, the inner lumen being configured to receive the suture lengths, the knot replacement element being at least partially positioned within the distal end of the barrel adjacent to the distal portion of the shaft and being configured to selectively fasten the suture lengths together over the vessel repair site;
    a snare having an elongate portion and a snare portion, the snare being configured to draw the suture lengths through the inner lumen of the knot replacement element and at least a portion of the elongate body; and
    a trimmer member configured to selectively trim the suture lengths extending proximal of the knot replacement element.

2. The system of claim 1, wherein the shaft includes an access lumen configured to receive the trimmer member and the snare, the trimmer member being slidably mounted within the access lumen, the access lumen extending between a first opening at the proximal end of the shaft and a second opening in the distal portion of the shaft.

3. The system of claim 2, wherein the distal portion of the shaft includes a ramped surface configured to guide the snare between an opening of the knot replacement element and the second opening of the access lumen.

4. The system of claim 2, wherein an opening of the knot replacement element and the second opening of the access lumen are offset.

5. The system of claim 2, wherein the snare is configured to draw the suture lengths proximally through the knot replacement element, into the second opening of the access lumen, and out of the first opening of the access lumen.

6. The system of claim 1, wherein the shaft is configured to selectively eject the knot replacement element from the barrel.

7. The system of claim 1, wherein the knot replacement element is moveable between a first position and a second position wherein the knot replacement element is fastened on the suture lengths.

8. The system of claim 7, wherein the shaft is configured to move the knot replacement element to the second position.

9. The system of claim 1, wherein the barrel includes one or more side ports formed in a wall of the barrel, each of the one or more side ports being in communication with the distal end of the barrel.

10. The system of claim 9, wherein the trimmer member is slidably mounted on the barrel, the trimmer member being moveable between a first position wherein a cutting element of the trimmer member is proximal to the one or more side ports of the barrel and a second position wherein the cutting element of the trimmer member is distal to the one or more side ports of the barrel.

11. The system of claim 1, wherein the knot replacement element comprises a coiled wire having a plurality of coils forming loops of varying diameters, the knot replacement element being moveable between a first position wherein the suture lengths may be looped in and out of the coils and a second position wherein the coils are compressed together to fasten the suture lengths between the coils.

12. The system of claim 11, wherein the shaft is configured to move the knot replacement element from the first position to the second position.

13. The system of claim 11, wherein the coils of the knot replacement element have friction producing elements.

14. The system of claim 1, wherein the knot replacement element comprises a ring having a proximal surface forming a locking edge, a distal surface, the opening of the knot replacement element being tapered and extending between the proximal surface and the distal surface.

15. The system of claim 14, wherein the suture lengths include steps formed therein, the steps being configured to lock on the locking edge of the knot replacement element when a proximal force is applied to the knot replacement element.

16. The system of claim 1, wherein an opening of the knot replacement element is cross-shaped.

17. The system of claim 1, further comprising a collet attached to the distal portion of the shaft, the collet being configured to selectively hold and crimp the knot replacement element onto the suture lengths over the repair site in body tissue.

18. The system of claim 17, wherein the collet comprises a pair of elongate members separated by a predetermined gap, the gap being configured to receive at least a portion of the knot replacement element, each of the pair of elongate members having a semi-circular portion having chambered edges.

19. The system of claim 17, wherein the distal end of the barrel includes a hollow conical portion associated with the collet, the conical portion being configured such that distal movement of the collet within the conical portion compresses the collet to crimp the knot replacement element onto the suture lengths.

20. The system of claim 17, further comprising an actuator configured to actuate the collet.

21. The system of claim 20, wherein the actuator comprises a cam lever.

22. The system of claim 1, wherein the trimmer member is attached to a rifled track formed in an outer surface of the barrel such that rotation of the trimmer member moves the trimmer along a longitudinal length of the barrel.

23. The system of claim 1, wherein the knot replacement element comprises a hollow tube having one or more indentations formed in a sidewall of the tube, each indentation having at least two edges separated from the sidewall of the tube.

24. The system of claim 23, further comprising a mandrel attached to the distal end of the shaft, the mandrel being configured to selectively force the indentation outward such that the suture lengths are pinched between the indentation and the sidewall of the tube.

25. The system of claim 1, wherein the knot replacement element comprises an elastic disc having an inner locking region and a outer base region, the inner locking region being at least partially defined by one or more slits extending between an upper surface and a lower surface of the elastic disc, the elastic disc being moveable between a first position wherein at least a portion of the inner locking region extends above the outer base region to form an opening in the elastic disc, the opening being configured to receive the suture lengths, and a second position wherein the inner locking region and the outer base region are biased toward a substantially common plane and configured to lock onto the suture lengths extending through the one or more slits.

26. The system of claim 1, wherein the knot replacement element further comprises:
 a ring having an inner lumen extending therethrough, the inner lumen being tapered between a proximal surface and a distal surface; and
 one or more sutures extending through the inner lumen of the ring, the one or more sutures having steps formed therein, the steps being configured to lock on the proximal surface of the ring when the one or more sutures are pulled distally relative to the ring.

27. The system of claim 1, wherein the knot replacement element is configured to have the suture lengths drawn through the one or more indentations, wherein the one or more indentations are configured to be bendable in order to selectively pinch the suture lengths between the one or more indentations and the sidewall of the tube.

28. A suture securing system for use in closing a vessel puncture site while eliminating the need for suture lengths to be manually tied in knots, the system comprising:
 an elongate body comprising a shaft having a proximal end and a distal portion and a barrel extending along at least a portion of the shaft, the barrel having a proximal end and a distal end, the distal end of the barrel having one or more side ports and a flared portion, the barrel comprising an opening, the barrel being mounted on the shaft such that the shaft can slide relative to the barrel, the elongate body being configured for insertion through a tissue tract to position the distal end of the barrel adjacent the vessel puncture site;
 a knot replacement element having an outer surface and an inner lumen extending therethrough, the inner lumen being configured to receive the suture lengths, the knot replacement element being at least partially positioned within the distal end of the barrel adjacent to the distal portion of the shaft and being configured to selectively fasten the suture lengths together over the vessel repair site;
 a collet connected to the distal portion of the shaft and disposed within the flared portion of the barrel, the collet comprising a pair of elongate members separated by a predetermined gap, the gap being configured to selectively receive the knot replacement element, the collet being moveable between a first position and a second position wherein the pair of elongate members are forced together by an inner surface of the flared portion to fasten the knot replacement element onto the suture lengths;
 a snare having an elongate portion and a snare portion, the snare being configured to draw the suture lengths through the inner lumen of the knot replacement element and through at least a portion of the elongate body;
 a trimmer member configured to selectively trim the suture lengths extending proximal of the knot replacement element; and
 an actuator operatively connected to the collet, the actuator being configured to move the collet between the first position and the second position.

29. The system of claim 28, further comprising a sheath surrounding at least a portion of the barrel, the sheath having a distal end comprising an opening, a side port, and a side lumen, the side lumen extending between the side port of the sheath and the distal end of the sheath, the snare being further configured to draw the suture lengths through at least a portion of the sheath.

30. The suture securing system of claim 26, wherein the knot replacement element comprises an elastic disc having an inner locking region and a outer base region, the inner locking region being at least partially defined by one or more slits extending between an upper surface and a lower surface of the elastic disc, the elastic disc being moveable between a first position wherein at least a portion of the inner locking region extends above the outer base region to form an opening in the elastic disc, the opening being configured to receive suture lengths, and a second position wherein the inner locking region and the outer base region are biased toward a substantially common plane and configured to lock onto the suture lengths extending through the one or more slits.

31. The suture securing system of claim 30 wherein the one or more slits include one or more friction elements.

32. The suture securing system of claim 31, wherein the one or more slits comprise a slit forming at least a part of a circle.

33. The suture securing system of claim 30, wherein the one or more slits comprise a pair of slits forming a cross.

34. A method for securing suture lengths over a vessel repair site after the suture lengths have been placed on opposing sides of a puncture in a vessel wall, while eliminating the need for suture lengths to be manually tied in knots, comprising:
 positioning a distal portion of an elongate body comprising a shaft and a barrel in proximity with a tissue tract, the shaft having a proximal end and a distal portion, the barrel having a proximal end and a distal end comprising an opening, the shaft being moveably disposed within the barrel, wherein a knot replacement element is positioned within a distal portion of the barrel adjacent the distal portion of the shaft, the knot replacement element having an outer surface and an inner lumen extending therethrough, the knot replacement element being at least partially positioned within the distal end of the barrel adjacent to the distal portion of the shaft and being configured to selectively fasten the suture lengths together over the vessel repair site;
 securing suture lengths to a snare extended through the knot replacement element and at least a portion of the barrel, the snare having an elongate portion and a snare portion;
 drawing the suture lengths through the inner lumen in the knot replacement element and at least a portion of the elongate body with the snare;
 advancing the shaft and the knot replacement element toward an outer surface of the vessel wall;
 tensioning the suture lengths to pull the puncture closed;
 securing the knot replacement element onto the suture lengths such that the suture lengths are substantially fixed relative to the vessel wall; and trimming the suture lengths extending proximal of the knot replacement element with a trimmer member associated with the barrel.

35. The method of claim 34, wherein securing the knot replacement element unto the suture lengths comprises crimping the knot replacement element with a collet, the collet being attached to the shaft.

36. The method of claim 35, further comprising actuating the collet with a cam lever attached to the barrel.

37. The method of claim 34, wherein securing the knot replacement element to the suture lengths comprises crushing the knot replacement element with the shaft.

* * * * *